United States Patent
Moreno, Jr. et al.

(10) Patent No.: US 8,870,747 B2
(45) Date of Patent: Oct. 28, 2014

(54) SCRAPING FLUID REMOVAL IN A SURGICAL ACCESS DEVICE

(75) Inventors: Cesar E. Moreno, Jr., Cincinnati, OH (US); Patrick J. Minnelli, Harrison, OH (US); Thomas A. Gilker, Cincinnati, OH (US); Daniel J. Mumaw, Cincinnati, OH (US); Rebecca J. Mollere, Cincinnati, OH (US); Randall Tanguay, Lebanon, OH (US); Daniel H. Duke, West Chester, OH (US); Paul H. Kistler, Fairfield, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1081 days.

(21) Appl. No.: 12/110,727

(22) Filed: Apr. 28, 2008

(65) Prior Publication Data
US 2009/0270681 A1 Oct. 29, 2009

(51) Int. Cl.
*A61B 1/00* (2006.01)
*A61M 5/178* (2006.01)
*A61B 1/12* (2006.01)
*A61B 17/34* (2006.01)

(52) U.S. Cl.
CPC .............. *A61B 17/3462* (2013.01); *A61B 1/126* (2013.01); *A61B 2017/3464* (2013.01); *A61B 2017/3437* (2013.01); *A61B 1/122* (2013.01); *A61B 17/3498* (2013.01)
USPC ..................................... 600/114; 604/167.02

(58) Field of Classification Search
USPC ......................... 600/104, 114, 154, 121–125; 604/167.01–167.06
See application file for complete search history.

(56) References Cited

U.S. PATENT DOCUMENTS

| 2,628,404 A | 2/1953 | Myers |
| 3,229,691 A | 1/1966 | Crowe, Jr. |
| 3,900,022 A | 8/1975 | Widran |
| 3,903,877 A | 9/1975 | Terada et al. |
| 3,924,608 A | 12/1975 | Mitsui et al. |
| 3,980,078 A | 9/1976 | Tominaga et al. |

(Continued)

FOREIGN PATENT DOCUMENTS

| CA | 2060930 | 10/1992 |
| CA | 2661238 A1 | 10/2009 |

(Continued)

OTHER PUBLICATIONS

International Search Report, from PCT/US10/42765, mailed Oct. 13, 2010.

(Continued)

*Primary Examiner* — Alireza Nia
(74) *Attorney, Agent, or Firm* — Mintz Levin Cohn Ferris Glovsky and Popeo, P.C.

(57) ABSTRACT

The present invention generally provides methods and devices for removing fluid from a surgical instrument. Surgical access devices and seal systems are generally provided having one or more valves or seal assemblies to create a closed system between the outside environment and the environment in which the surgical access device is being inserted. In one embodiment, a seal assembly is provided and can include a seal having an opening configured to receive a surgical instrument therethrough and a fluid remover in the form of an absorbent element, a scraper element, a wicking element, or any combination thereof can be associated with the seal and configured to remove fluid from the opening and/or a surgical instrument.

27 Claims, 28 Drawing Sheets

(56) References Cited

U.S. PATENT DOCUMENTS

| | | |
|---|---|---|
| 3,981,276 A | 9/1976 | Ernest |
| 4,204,563 A | 5/1980 | Pyle |
| 4,279,246 A | 7/1981 | Chikama et al. |
| 4,281,646 A | 8/1981 | Kinoshita |
| 4,335,721 A | 6/1982 | Matthews |
| 4,651,517 A | 3/1987 | Benhamou et al. |
| 4,687,033 A | 8/1987 | Furrow et al. |
| 4,690,140 A | 9/1987 | Mecca |
| 4,722,000 A | 1/1988 | Chatenever |
| 4,836,187 A | 6/1989 | Iwakoshi et al. |
| 4,844,052 A | 7/1989 | Iwakoshi et al. |
| 4,847,364 A | 7/1989 | Mockli |
| 4,877,016 A | 10/1989 | Kantor et al. |
| 4,919,305 A | 4/1990 | Podgers |
| 4,929,235 A * | 5/1990 | Merry et al. ............. 604/167.04 |
| 4,934,135 A | 6/1990 | Rozenwasser |
| 4,942,867 A | 7/1990 | Takahashi et al. |
| 4,943,280 A | 7/1990 | Lander |
| 4,958,970 A | 9/1990 | Rose et al. |
| 4,960,412 A | 10/1990 | Fink |
| 5,000,745 A * | 3/1991 | Guest et al. ................... 604/256 |
| 5,084,057 A | 1/1992 | Green et al. |
| 5,104,383 A | 4/1992 | Shichman |
| 5,112,308 A | 5/1992 | Olsen et al. |
| 5,127,909 A | 7/1992 | Shichman |
| 5,167,220 A | 12/1992 | Brown |
| 5,180,373 A | 1/1993 | Green et al. |
| 5,191,878 A | 3/1993 | Iida et al. |
| 5,197,955 A | 3/1993 | Stephens et al. |
| 5,201,714 A | 4/1993 | Gentelia et al. |
| 5,207,213 A | 5/1993 | Auhll et al. |
| 5,209,737 A | 5/1993 | Ritchart et al. |
| 5,226,891 A | 7/1993 | Bushatz et al. |
| 5,237,984 A | 8/1993 | Williams, III et al. |
| 5,242,412 A | 9/1993 | Blake, III |
| 5,256,149 A | 10/1993 | Banik et al. |
| 5,279,542 A | 1/1994 | Wilk |
| 5,308,336 A | 5/1994 | Hart et al. |
| 5,312,351 A | 5/1994 | Gerrone |
| 5,312,363 A | 5/1994 | Ryan et al. |
| 5,312,397 A | 5/1994 | Cosmescu |
| 5,313,934 A | 5/1994 | Wiita et al. |
| 5,320,608 A | 6/1994 | Gerrone |
| 5,320,610 A | 6/1994 | Yoon |
| 5,326,013 A | 7/1994 | Green et al. |
| 5,330,437 A | 7/1994 | Durman |
| 5,334,164 A | 8/1994 | Guy et al. |
| 5,337,730 A | 8/1994 | Maguire |
| 5,339,800 A | 8/1994 | Wiita et al. |
| 5,342,315 A | 8/1994 | Rowe et al. |
| 5,347,988 A | 9/1994 | Hori |
| 5,354,302 A | 10/1994 | Ko |
| 5,364,002 A | 11/1994 | Green et al. |
| 5,369,525 A | 11/1994 | Bala et al. |
| 5,370,656 A | 12/1994 | Shevel |
| 5,377,669 A | 1/1995 | Schulz |
| 5,382,297 A | 1/1995 | Valentine et al. |
| 5,386,817 A | 2/1995 | Jones |
| 5,387,197 A | 2/1995 | Smith et al. |
| 5,389,081 A | 2/1995 | Castro |
| 5,391,154 A | 2/1995 | Young |
| 5,392,766 A * | 2/1995 | Masterson et al. ............ 600/157 |
| 5,395,342 A | 3/1995 | Yoon |
| 5,400,767 A | 3/1995 | Murdoch et al. |
| 5,407,433 A * | 4/1995 | Loomas ................... 604/167.06 |
| 5,419,309 A | 5/1995 | Biehl |
| 5,419,311 A | 5/1995 | Yabe et al. |
| 5,441,513 A | 8/1995 | Roth |
| 5,443,452 A | 8/1995 | Hart et al. |
| 5,448,990 A | 9/1995 | De Faria-Correa et al. |
| 5,449,370 A | 9/1995 | Vaitekunas |
| 5,458,633 A | 10/1995 | Bailey |
| 5,458,640 A | 10/1995 | Gerrone |
| 5,462,100 A | 10/1995 | Covert et al. |
| 5,464,008 A | 11/1995 | Kim |
| 5,476,475 A | 12/1995 | Gadberry |
| 5,486,154 A | 1/1996 | Kelleher |
| 5,492,304 A | 2/1996 | Smith et al. |
| 5,496,142 A | 3/1996 | Fodor et al. |
| 5,496,280 A | 3/1996 | Vandenbroek et al. |
| 5,496,345 A | 3/1996 | Kieturakis et al. |
| 5,496,411 A | 3/1996 | Candy et al. |
| 5,514,084 A | 5/1996 | Fisher |
| 5,514,153 A | 5/1996 | Bonutti |
| 5,518,026 A | 5/1996 | Benjey |
| 5,518,502 A | 5/1996 | Kaplan et al. |
| 5,522,833 A | 6/1996 | Stephens et al. |
| 5,533,496 A | 7/1996 | De Faria-Correa et al. |
| 5,535,759 A | 7/1996 | Wilk |
| 5,536,234 A | 7/1996 | Newman |
| 5,542,931 A | 8/1996 | Gravener et al. |
| 5,545,142 A | 8/1996 | Stephens et al. |
| 5,545,179 A | 8/1996 | Williamson, IV |
| 5,549,543 A | 8/1996 | Kim |
| 5,551,448 A | 9/1996 | Matula et al. |
| 5,554,151 A | 9/1996 | Hinchliffe |
| 5,568,828 A | 10/1996 | Harris |
| 5,569,183 A | 10/1996 | Kieturakis |
| 5,569,205 A | 10/1996 | Hart et al. |
| 5,575,756 A | 11/1996 | Karasawa et al. |
| 5,584,850 A | 12/1996 | Hart et al. |
| 5,590,697 A | 1/1997 | Benjey et al. |
| 5,591,192 A | 1/1997 | Privitera et al. |
| 5,603,702 A | 2/1997 | Smith et al. |
| 5,605,175 A | 2/1997 | Bergsma et al. |
| 5,628,732 A | 5/1997 | Antoon, Jr. et al. |
| 5,630,795 A | 5/1997 | Kuramoto et al. |
| 5,630,813 A | 5/1997 | Kieturakis |
| 5,634,911 A | 6/1997 | Hermann et al. |
| 5,643,227 A * | 7/1997 | Stevens ......................... 604/264 |
| 5,643,301 A | 7/1997 | Mollenauer |
| 5,647,372 A | 7/1997 | Tovey et al. |
| 5,647,840 A | 7/1997 | D'Amelio et al. |
| 5,651,757 A | 7/1997 | Meckstroth |
| 5,658,273 A | 8/1997 | Long |
| 5,662,614 A | 9/1997 | Edoga |
| 5,685,823 A | 11/1997 | Ito et al. |
| 5,688,222 A | 11/1997 | Hluchy et al. |
| 5,709,664 A | 1/1998 | Vandenbroek et al. |
| 5,720,756 A | 2/1998 | Green et al. |
| 5,720,759 A | 2/1998 | Green et al. |
| 5,725,477 A | 3/1998 | Yasui et al. |
| 5,725,478 A | 3/1998 | Saad |
| 5,743,884 A * | 4/1998 | Hasson et al. ........... 604/167.02 |
| 5,752,938 A | 5/1998 | Flatland et al. |
| 5,755,252 A | 5/1998 | Bergsma et al. |
| 5,755,732 A | 5/1998 | Green et al. |
| 5,776,112 A | 7/1998 | Stephens et al. |
| 5,782,751 A | 7/1998 | Matsuno |
| 5,782,859 A | 7/1998 | Nicholas et al. |
| 5,788,676 A | 8/1998 | Yoon |
| 5,792,044 A | 8/1998 | Foley et al. |
| 5,792,113 A | 8/1998 | Kramer et al. |
| 5,797,434 A | 8/1998 | Benjey et al. |
| 5,807,338 A | 9/1998 | Smith et al. |
| 5,814,026 A | 9/1998 | Yoon |
| D399,316 S | 10/1998 | Molina |
| 5,817,061 A | 10/1998 | Goodwin et al. |
| 5,820,600 A | 10/1998 | Carlson et al. |
| 5,842,971 A | 12/1998 | Yoon |
| 5,848,992 A | 12/1998 | Hart et al. |
| 5,860,458 A | 1/1999 | Benjey et al. |
| 5,871,440 A | 2/1999 | Okada et al. |
| 5,882,345 A | 3/1999 | Yoon |
| 5,895,377 A * | 4/1999 | Smith et al. ................... 604/256 |
| 5,902,231 A | 5/1999 | Foley et al. |
| 5,902,264 A | 5/1999 | Toso et al. |
| 5,906,595 A | 5/1999 | Powell et al. |
| 5,906,598 A | 5/1999 | Giesler et al. |
| 5,944,654 A | 8/1999 | Crawford |
| 5,954,635 A | 9/1999 | Foley et al. |
| 5,957,888 A | 9/1999 | Hinchliffe |
| 5,961,505 A | 10/1999 | Coe et al. |
| 5,964,781 A | 10/1999 | Mollenauer et al. |

(56) References Cited

U.S. PATENT DOCUMENTS

| | | |
|---|---|---|
| 5,983,958 A | 11/1999 | Bergsma et al. |
| 5,989,183 A | 11/1999 | Reisdorf et al. |
| 5,989,224 A | 11/1999 | Exline et al. |
| 5,993,380 A | 11/1999 | Yabe et al. |
| 6,004,326 A | 12/1999 | Castro et al. |
| 6,007,487 A | 12/1999 | Foley et al. |
| 6,017,333 A | 1/2000 | Bailey |
| D425,619 S | 5/2000 | Bierman |
| 6,062,276 A | 5/2000 | Benjey et al. |
| 6,063,050 A | 5/2000 | Manna et al. |
| 6,110,103 A | 8/2000 | Donofrio |
| 6,126,592 A | 10/2000 | Proch et al. |
| 6,152,871 A | 11/2000 | Foley et al. |
| 6,159,182 A | 12/2000 | Davis et al. |
| 6,162,170 A | 12/2000 | Foley et al. |
| 6,167,920 B1 | 1/2001 | Enge |
| 6,176,823 B1 | 1/2001 | Foley et al. |
| 6,176,825 B1 | 1/2001 | Chin et al. |
| 6,206,057 B1 | 3/2001 | Benjey et al. |
| 6,206,822 B1 | 3/2001 | Foley et al. |
| 6,216,661 B1 | 4/2001 | Pickens et al. |
| 6,217,509 B1 | 4/2001 | Foley et al. |
| 6,253,802 B1 | 7/2001 | Enge |
| 6,258,025 B1 | 7/2001 | Swallert |
| 6,258,065 B1 | 7/2001 | Dennis et al. |
| 6,264,604 B1 | 7/2001 | Kieturakis et al. |
| 6,287,313 B1 | 9/2001 | Sasso |
| 6,354,992 B1 | 3/2002 | Kato |
| 6,371,909 B1 | 4/2002 | Hoeg et al. |
| 6,409,657 B1 | 6/2002 | Kawano et al. |
| 6,423,266 B1 | 7/2002 | Choperena et al. |
| 6,425,535 B1 | 7/2002 | Akiba et al. |
| 6,425,859 B1 | 7/2002 | Foley et al. |
| 6,443,190 B1 | 9/2002 | Enge |
| 6,447,446 B1 | 9/2002 | Smith et al. |
| 6,482,181 B1 | 11/2002 | Racenet et al. |
| 6,494,893 B2 | 12/2002 | Dubrul et al. |
| 6,497,687 B1 | 12/2002 | Blanco |
| 6,516,835 B2 | 2/2003 | Enge |
| 6,520,907 B1 | 2/2003 | Foley et al. |
| 6,534,002 B1 | 3/2003 | Lin et al. |
| 6,551,282 B1 | 4/2003 | Exline et al. |
| 6,562,046 B2 | 5/2003 | Sasso |
| 6,569,120 B1 | 5/2003 | Green et al. |
| 6,595,915 B2 | 7/2003 | Akiba et al. |
| 6,595,946 B1 * | 7/2003 | Pasqualucci .................... 604/27 |
| 6,601,617 B2 | 8/2003 | Enge |
| 6,605,098 B2 | 8/2003 | Nobis et al. |
| 6,638,214 B2 | 10/2003 | Akiba et al. |
| 6,648,906 B2 | 11/2003 | Lasheras et al. |
| 6,668,418 B2 | 12/2003 | Bastien |
| 6,679,833 B2 | 1/2004 | Smith et al. |
| 6,679,834 B2 | 1/2004 | Stahl et al. |
| 6,679,837 B2 | 1/2004 | Daikuzono |
| 6,685,665 B2 | 2/2004 | Booth et al. |
| 6,699,185 B2 | 3/2004 | Gminder et al. |
| 6,702,787 B2 | 3/2004 | Racenet et al. |
| 6,712,757 B2 | 3/2004 | Becker et al. |
| 6,726,663 B1 | 4/2004 | Dennis |
| 6,755,782 B2 | 6/2004 | Ogawa et al. |
| 6,860,869 B2 | 3/2005 | Dennis |
| 6,860,892 B1 | 3/2005 | Tanaka et al. |
| 6,873,409 B1 | 3/2005 | Slater |
| 6,916,286 B2 | 7/2005 | Kazakevich |
| 6,918,924 B2 | 7/2005 | Lasheras et al. |
| 6,923,759 B2 | 8/2005 | Kasahara et al. |
| 6,942,671 B1 | 9/2005 | Smith |
| 6,976,957 B1 | 12/2005 | Chin et al. |
| 6,981,966 B2 | 1/2006 | Green et al. |
| 6,989,003 B2 | 1/2006 | Wing et al. |
| 7,008,416 B2 | 3/2006 | Sakaguchi et al. |
| 7,025,747 B2 | 4/2006 | Smith |
| 7,052,454 B2 | 5/2006 | Taylor |
| 7,056,303 B2 | 6/2006 | Dennis et al. |
| 7,056,321 B2 | 6/2006 | Pagliuca et al. |
| 7,060,025 B2 | 6/2006 | Long et al. |
| 7,077,803 B2 | 7/2006 | Kasahara et al. |
| 7,083,626 B2 | 8/2006 | Hart et al. |
| 7,104,657 B2 | 9/2006 | Sherwin et al. |
| 7,105,009 B2 | 9/2006 | Johnson et al. |
| 7,112,185 B2 | 9/2006 | Hart et al. |
| 7,163,525 B2 | 1/2007 | Franer |
| 7,169,130 B2 | 1/2007 | Exline et al. |
| D541,417 S | 4/2007 | Albrecht et al. |
| 7,198,598 B2 | 4/2007 | Smith et al. |
| 7,207,347 B2 | 4/2007 | Olshanetsky et al. |
| 7,244,244 B2 | 7/2007 | Racenet et al. |
| D555,788 S | 11/2007 | Southwell et al. |
| 7,309,469 B2 * | 12/2007 | Anderson et al. ............ 422/550 |
| 7,344,519 B2 | 3/2008 | Wing et al. |
| D567,372 S | 4/2008 | Chesnin |
| 7,371,227 B2 | 5/2008 | Zeiner |
| D573,255 S | 7/2008 | Stephens |
| 7,444,801 B2 | 11/2008 | Rosenwasser et al. |
| 7,473,243 B2 | 1/2009 | Dennis et al. |
| D589,617 S | 3/2009 | Carter |
| 7,507,210 B2 | 3/2009 | Hibner et al. |
| 7,591,802 B2 | 9/2009 | Johnson et al. |
| 7,717,412 B2 | 5/2010 | Anzai |
| 7,785,294 B2 | 8/2010 | Hueil et al. |
| 7,981,092 B2 | 7/2011 | Duke |
| 8,075,528 B2 | 12/2011 | Widenhouse et al. |
| D652,509 S | 1/2012 | Kyvik et al. |
| 8,206,357 B2 | 6/2012 | Bettuchi |
| 8,206,376 B2 | 6/2012 | Barron et al. |
| 8,273,060 B2 | 9/2012 | Moreno, Jr. et al. |
| 8,292,854 B2 * | 10/2012 | Brockmeier et al. .... 604/167.06 |
| 8,328,768 B2 | 12/2012 | Quigley et al. |
| 8,551,058 B2 | 10/2013 | Measamer et al. |
| 8,568,362 B2 | 10/2013 | Moreno, Jr. et al. |
| 2002/0022762 A1 | 2/2002 | Beane et al. |
| 2002/0065450 A1 | 5/2002 | Ogawa |
| 2002/0068923 A1 | 6/2002 | Caldwell et al. |
| 2002/0103420 A1 | 8/2002 | Coleman et al. |
| 2002/0107484 A1 | 8/2002 | Dennis et al. |
| 2002/0161387 A1 | 10/2002 | Blanco |
| 2003/0004529 A1 | 1/2003 | Tsonton et al. |
| 2003/0060770 A1 | 3/2003 | Wing et al. |
| 2003/0130674 A1 | 7/2003 | Kasahara et al. |
| 2003/0135942 A1 | 7/2003 | Bastien |
| 2003/0139756 A1 | 7/2003 | Brustad |
| 2003/0195472 A1 * | 10/2003 | Green et al. ............ 604/167.04 |
| 2003/0208104 A1 | 11/2003 | Carrillo et al. |
| 2004/0034339 A1 | 2/2004 | Stoller et al. |
| 2004/0106942 A1 | 6/2004 | Taylor et al. |
| 2004/0167559 A1 | 8/2004 | Taylor et al. |
| 2004/0171990 A1 | 9/2004 | Dennis et al. |
| 2004/0220452 A1 | 11/2004 | Shalman |
| 2004/0230161 A1 | 11/2004 | Zeiner |
| 2004/0256004 A1 | 12/2004 | Kessell et al. |
| 2004/0260244 A1 | 12/2004 | Piechowicz et al. |
| 2005/0033342 A1 | 2/2005 | Hart et al. |
| 2005/0043683 A1 | 2/2005 | Ravo |
| 2005/0059865 A1 | 3/2005 | Kahle et al. |
| 2005/0059934 A1 | 3/2005 | Wenchell et al. |
| 2005/0070850 A1 | 3/2005 | Albrecht |
| 2005/0070946 A1 | 3/2005 | Franer et al. |
| 2005/0070947 A1 | 3/2005 | Franer et al. |
| 2005/0077688 A1 | 4/2005 | Voegele et al. |
| 2005/0077689 A1 | 4/2005 | Hueil |
| 2005/0096605 A1 | 5/2005 | Green et al. |
| 2005/0131349 A1 | 6/2005 | Albrecht et al. |
| 2005/0165277 A1 | 7/2005 | Carrillo et al. |
| 2005/0203467 A1 * | 9/2005 | O'Heeron et al. ............ 604/249 |
| 2005/0203543 A1 | 9/2005 | Hilal et al. |
| 2005/0216028 A1 | 9/2005 | Hart et al. |
| 2005/0222582 A1 | 10/2005 | Wenchell |
| 2005/0241647 A1 | 11/2005 | Nguyen et al. |
| 2005/0267419 A1 | 12/2005 | Smith |
| 2005/0288622 A1 | 12/2005 | Albrecht et al. |
| 2006/0020165 A1 | 1/2006 | Adams |
| 2006/0047240 A1 | 3/2006 | Kumar et al. |
| 2006/0052666 A1 | 3/2006 | Kumar et al. |
| 2006/0068360 A1 | 3/2006 | Boulais |

(56) References Cited

U.S. PATENT DOCUMENTS

| | | | |
|---|---|---|---|
| 2006/0069306 A1 | 3/2006 | Banik et al. | |
| 2006/0069312 A1 | 3/2006 | O'Connor | |
| 2006/0100485 A1 | 5/2006 | Arai et al. | |
| 2006/0122556 A1 | 6/2006 | Kumar et al. | |
| 2006/0122557 A1 | 6/2006 | Kumar et al. | |
| 2006/0129098 A1 | 6/2006 | Hart et al. | |
| 2006/0135972 A1 | 6/2006 | Zeiner | |
| 2006/0135977 A1 | 6/2006 | Thompson et al. | |
| 2006/0135978 A1 | 6/2006 | Franer | |
| 2006/0149137 A1 | 7/2006 | Pingleton et al. | |
| 2006/0199998 A1 | 9/2006 | Akui et al. | |
| 2006/0211916 A1 | 9/2006 | Kasahara et al. | |
| 2006/0224121 A1 | 10/2006 | Hart et al. | |
| 2006/0224164 A1 | 10/2006 | Hart et al. | |
| 2006/0229565 A1 | 10/2006 | Dennis et al. | |
| 2006/0235455 A1 | 10/2006 | Oshida | |
| 2006/0264991 A1* | 11/2006 | Johnson et al. | 606/167 |
| 2006/0276688 A1 | 12/2006 | Surti | |
| 2006/0293559 A1 | 12/2006 | Grice et al. | |
| 2007/0005087 A1 | 1/2007 | Smith et al. | |
| 2007/0021713 A1 | 1/2007 | Kumar et al. | |
| 2007/0027453 A1 | 2/2007 | Hart et al. | |
| 2007/0088275 A1 | 4/2007 | Stearns et al. | |
| 2007/0088277 A1 | 4/2007 | McGinley et al. | |
| 2007/0129719 A1 | 6/2007 | Kendale et al. | |
| 2007/0142709 A1 | 6/2007 | Martone et al. | |
| 2007/0149931 A1 | 6/2007 | Cannon et al. | |
| 2007/0149993 A1 | 6/2007 | Kasahara et al. | |
| 2007/0185453 A1 | 8/2007 | Michael et al. | |
| 2007/0191759 A1 | 8/2007 | Stoller et al. | |
| 2007/0204890 A1 | 9/2007 | Torii | |
| 2007/0225556 A1 | 9/2007 | Ortiz et al. | |
| 2007/0225566 A1 | 9/2007 | Kawanishi | |
| 2007/0244361 A1 | 10/2007 | Ikeda et al. | |
| 2008/0009797 A1 | 1/2008 | Stellon et al. | |
| 2008/0009832 A1 | 1/2008 | Barron et al. | |
| 2008/0091143 A1 | 4/2008 | Taylor et al. | |
| 2008/0249475 A1 | 10/2008 | Albrecht et al. | |
| 2008/0269696 A1 | 10/2008 | Exline et al. | |
| 2008/0294113 A1 | 11/2008 | Brockmeier et al. | |
| 2009/0005799 A1 | 1/2009 | Franer et al. | |
| 2009/0093682 A1 | 4/2009 | Izzo et al. | |
| 2009/0137943 A1 | 5/2009 | Stearns et al. | |
| 2009/0192444 A1 | 7/2009 | Albrecht et al. | |
| 2009/0221960 A1 | 9/2009 | Albrecht et al. | |
| 2009/0234293 A1 | 9/2009 | Albrecht et al. | |
| 2009/0240204 A1 | 9/2009 | Taylor et al. | |
| 2009/0264703 A1 | 10/2009 | Pribanic | |
| 2009/0270681 A1 | 10/2009 | Moreno et al. | |
| 2009/0270685 A1 | 10/2009 | Moreno et al. | |
| 2009/0270813 A1 | 10/2009 | Moreno, Jr. et al. | |
| 2009/0270817 A1 | 10/2009 | Moreno et al. | |
| 2009/0281478 A1 | 11/2009 | Duke | |
| 2009/0314422 A1 | 12/2009 | Racenet et al. | |
| 2010/0022958 A1 | 1/2010 | Moreno, Jr. et al. | |
| 2010/0211049 A1 | 8/2010 | Schertiger et al. | |
| 2011/0046449 A1 | 2/2011 | Minnelli et al. | |
| 2012/0140494 A1 | 6/2012 | Gu et al. | |
| 2012/0330099 A1 | 12/2012 | Moreno et al. | |

FOREIGN PATENT DOCUMENTS

| | | |
|---|---|---|
| DE | 19619065 A1 | 11/1997 |
| DE | 10330518 A1 | 2/2005 |
| EP | 0517248 | 12/1992 |
| EP | 0567142 | 10/1993 |
| EP | 568383 A1 | 11/1993 |
| EP | 570802 A1 | 11/1993 |
| EP | 0570802 A1 | 11/1993 |
| EP | 664101 A1 | 7/1995 |
| EP | 0696459 | 2/1996 |
| EP | 731718 B1 | 9/1996 |
| EP | 845960 B1 | 6/1998 |
| EP | 875256 B1 | 11/1998 |
| EP | 890342 B1 | 1/1999 |
| EP | 898971 B1 | 3/1999 |
| EP | 0972493 | 1/2000 |
| EP | 1210904 B1 | 6/2002 |
| EP | 1284664 | 2/2003 |
| EP | 1312318 B1 | 5/2003 |
| EP | 1323373 A3 | 7/2003 |
| EP | 1348386 | 10/2003 |
| EP | 1459688 | 9/2004 |
| EP | 1629787 A2 | 3/2006 |
| EP | 1679043 | 7/2006 |
| EP | 1698291 | 9/2006 |
| EP | 1707133 | 10/2006 |
| EP | 1707135 A1 | 10/2006 |
| EP | 1709918 | 10/2006 |
| EP | 1834571 A1 | 9/2007 |
| EP | 1834573 A1 | 9/2007 |
| EP | 1994895 A1 | 11/2008 |
| GB | 2298906 A | 9/1996 |
| JP | 61036718 A2 | 2/1986 |
| JP | 3106329 A2 | 5/1991 |
| JP | 4020324 A2 | 1/1992 |
| JP | 4158825 A2 | 6/1992 |
| JP | 4170929 A2 | 6/1992 |
| JP | 4329510 A2 | 11/1992 |
| JP | 5192294 A2 | 8/1993 |
| JP | 5199979 A2 | 8/1993 |
| JP | 5207962 A2 | 8/1993 |
| JP | 6133927 A2 | 5/1994 |
| JP | 6169879 A2 | 6/1994 |
| JP | 6304121 A2 | 11/1994 |
| JP | 7178039 A2 | 7/1995 |
| JP | 7246187 A2 | 9/1995 |
| JP | 7289501 A2 | 11/1995 |
| JP | 7313442 A2 | 12/1995 |
| JP | 8154888 A2 | 6/1996 |
| JP | 8173372 A2 | 7/1996 |
| JP | 08-285001 A | 11/1996 |
| JP | 10043128 A2 | 2/1998 |
| JP | 11146882 A2 | 6/1999 |
| JP | 2002224014 B2 | 8/2002 |
| JP | 2002238906 A2 | 8/2002 |
| JP | 2002282274 A | 10/2002 |
| JP | 2003284686 A2 | 10/2003 |
| JP | 2004016455 A2 | 1/2004 |
| JP | 2004267583 A2 | 9/2004 |
| JP | 2005253543 A2 | 9/2005 |
| JP | 2005319101 A2 | 11/2005 |
| JP | 2007117289 A | 5/2007 |
| JP | 3151790 U | 6/2009 |
| JP | 2009261923 A | 11/2009 |
| RU | 2014032 C1 | 6/1994 |
| WO | 9407552 | 4/1994 |
| WO | 9532019 | 11/1995 |
| WO | 9604946 A1 | 2/1996 |
| WO | 9740759 A1 | 11/1997 |
| WO | 9809673 A1 | 3/1998 |
| WO | 0189371 A1 | 11/2001 |
| WO | 02078527 A2 | 10/2002 |
| WO | 02096307 A2 | 12/2002 |
| WO | 03011154 A2 | 2/2003 |
| WO | 2004043275 A1 | 5/2004 |
| WO | 2005016133 A1 | 2/2005 |
| WO | 2005030293 A2 | 4/2005 |
| WO | 2005097019 A2 | 10/2005 |
| WO | 2005097234 A2 | 10/2005 |
| WO | 2008093313 A1 | 8/2008 |
| WO | 2009005986 A1 | 1/2009 |

OTHER PUBLICATIONS

European Search Report dated Aug. 13, 2009 for EP App. No. 09 251 201.

European Search Report dated Aug. 11, 2009 for EP App. No. 09 251 208.

U.S. Appl. No. 11/771,263 for "Duckbill Seal with Fluid Drainage Feature," filed Jun. 29, 2007, Paul Franer et al.

European Search Report issued Aug. 11, 2009 for Application No. 09251196.3 (7 pages).

(56) References Cited

OTHER PUBLICATIONS

European Search Report issued Aug. 12, 2009 for Application No. 09251210.2 (8 pages).
U.S. Office Action issued May 30, 2013 for U.S. Appl. No. 29/403,077 (10 Pages).
Extended European Search Report for App. No. 12173272.1, dated Jul. 19, 2012 (7 pages).
Extended European Search Report for App. No. 12173277.0, dated Jul. 18, 2012 (6 pages).
Extended European Search Report for App. No. 12173283.8, dated Jul. 18, 2012 (6 pages).
Extended European Search Report for App. No. 12173290.3, dated Jul. 18, 2012 (7 pages).
International Search Report and Written Opinion for Application No. PCT/US2011/055905, mailed Jan. 11, 2012 (11 pages).

* cited by examiner

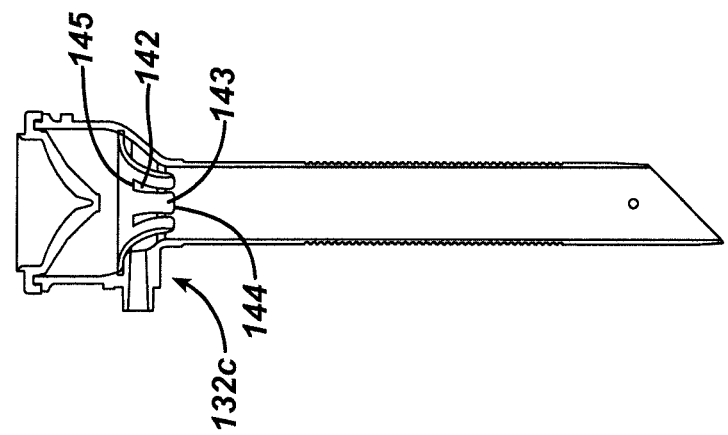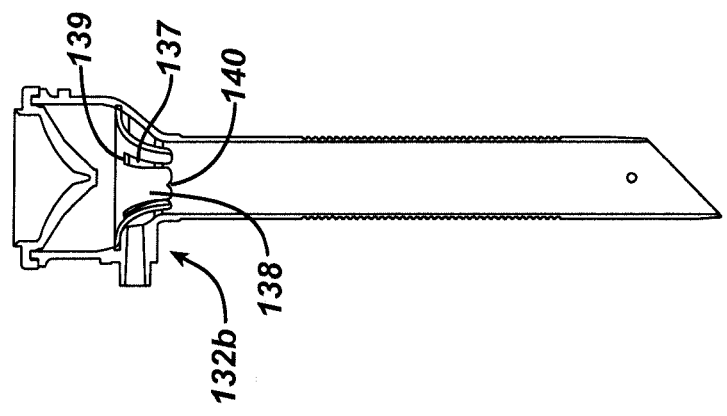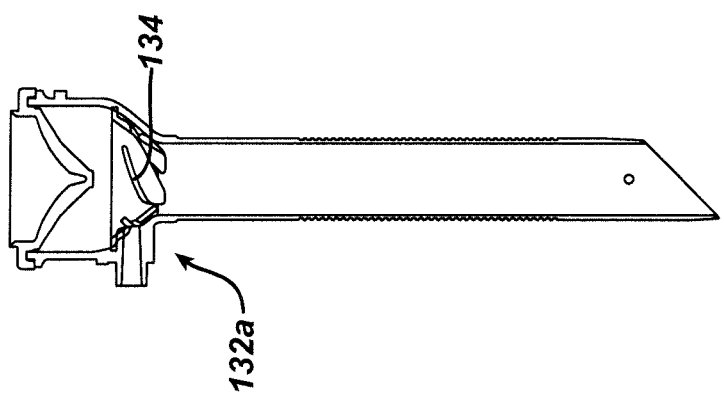

SCRAPING FLUID REMOVAL IN A SURGICAL ACCESS DEVICE

FIELD OF THE INVENTION

The present invention relates to methods and devices for performing surgical procedures, and in particular to methods and devices for maintaining visibility during surgical procedures.

BACKGROUND OF THE INVENTION

During laparoscopic surgery, one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. During such procedures, a scoping device, such as an endoscope or laparoscope, is inserted through one of the trocars to allow a surgeon to view the operative field on an external monitor coupled to the scoping device.

Scoping devices are often inserted and removed through a trocar multiple times during a single surgical procedure, and during each insertion and each removal they can encounter fluid that can adhere to the scopes lens and fully or partially impede visibility through the lens. Furthermore, a scope can draw fluid from inside or outside a patients body into the trocar, where the fluid can be deposited within the trocar until the scope or other instrument is reinserted through the trocar. Upon reinsertion, fluid can adhere to the scopes lens. The scopes lens thus needs to be cleaned to restore visibility, often multiple times during a single surgical procedure. With limited access to a scope in a body, each lens cleaning can require removing the scope from the body, cleaning the scope lens of fluid, and reintroducing the scope into the body. Such lens cleaning is a time-consuming procedure that also increases the chances of complications and contamination through repeated scope insertion and removal.

Accordingly, there is a need for methods and devices for maintaining clear visibility through a lens of a scoping device during a surgical procedure.

SUMMARY OF THE INVENTION

The present invention generally provides methods and devices for preventing fluid deposit onto and/or for removing fluid from a surgical instrument. In one embodiment, a seal assembly for use in a surgical access device is provided having a seal including a proximal flange with a sidewall extending distally therefrom and selectively movable between an open position when an instrument is disposed therethrough and a sealed closed position when no instrument is disposed therethrough. A fluid remover can be positioned adjacent to a distal end of the seal and it can be configured to remove fluid from a surgical instrument passed through the seal. The fluid remover can have various configurations and in one embodiment the fluid remover can include one or any combination of an absorbent for absorbing fluid, a scraper for scraping fluid, and a wicking element for wicking fluid.

In one exemplary embodiment, the fluid remover can include a substantially planar scraper having an opening formed therethrough and configured to scrape fluid off of a surgical instrument passed through the opening. In another embodiment, the scraper can include a plurality of channels formed therein and extending from the opening to an outer perimeter thereof for wicking fluid away from the opening. The fluid remover can further include an absorbent element disposed adjacent to the scraper and configured to absorb and wick fluid scraped off of a surgical instrument by the scraper. The absorbent element can also extend distally from the scraper. While the scraper and absorbent can have various shapes, in one embodiment the scraper is substantially circumferential and the absorbent is semi-circular. In other aspects, the scraper and absorbent element can be disposed within a cartridge.

In another embodiment, the absorbent element can include a first absorbent wick configured to absorb and wick fluid away from the scraper, and a second absorbent wick configured to absorb fluid from the first absorbent wick. The scraper can also includes a wicking element configured to wick fluid scraped off of an instrument by the scraper toward the absorbent.

In another exemplary embodiment, a surgical access device is provided and can include a housing defining a working channel extending therethrough that is sized and configured to receive a surgical instrument. In one exemplary embodiment, the access device can be a trocar and the housing can include a cannula extending distally therefrom. A seal can be disposed within the housing and configured to seal the working channel when no surgical instrument is disposed therethrough. The seal can also optionally be configured to form a seal around a surgical instrument disposed therethrough, or the housing can include a second seal that forms a seal around a surgical instrument disposed therethrough, but does not form a seal when no instrument is disposed therethrough. A fluid remover can be positioned distal of the seal and it can be configured to remove fluid from a surgical instrument passed through the seal. In one embodiment, the fluid remover can include one or any combination of an absorbent for absorbing fluid, a scraper for scraping fluid, and a wicking element for wicking fluid.

The fluid remover can be positioned at various locations within the housing, but in one embodiment the fluid remover is disposed within the housing adjacent to a distal surface of the seal. The fluid remover can include a scraper and an absorbent positioned distal of the scraper. The scraper can also include a wicking element configured to wick fluid away from the scraper. In an exemplary embodiment, the wicking element can include a plurality of channels formed in a distal surface of the scraper and extending radially outward from an opening formed in the scraper for receiving and scraping fluid off of a surgical instrument passed therethrough. The wicking element can include an absorbent wick in contact with a distal surface of the scraper and disposed radially outward from an opening formed in the scraper for receiving and scraping fluid off of a surgical instrument passed therethrough. The scraper can have various configurations. For example, the scraper can be a substantially circumferential member having an opening extending therethrough. In one embodiment, the scraper and absorbent can be contained within a cartridge disposed within the housing. In certain exemplary embodiments, the cartridge can include a protective wall configured to prevent contact between the absorbent and a surgical instrument passed through the trocar. The cartridge can also include a reservoir for collecting fluid that is scraped by the scraper.

Methods for removing fluid from a surgical access device are also provided and can include passing a surgical instrument through a seal in a working channel of a surgical access device extending into a body cavity, the seal moving from a sealed, closed position in which the working channel is sealed to an open position when the surgical instrument is passed therethrough. A fluid remover disposed distal of the seal can remove fluid from the surgical instrument to prevent fluid from being deposited on the seal. In one embodiment, the fluid remover can include a scraper that scrapes fluid off of the surgical instrument as the surgical instrument is passed through the surgical access device. The fluid remover can further include an absorbent that absorbs fluid off of the scraper. The surgical instrument can be passed through an opening in the scraper that scrapes fluid off of the surgical instrument. In another embodiment, the fluid remover can further include a wicking element that wicks fluid away from the opening in the scraper. The method can also include viewing the body cavity using a camera disposed on a distal end of the surgical instrument.

In another embodiment, a seal assembly for use in a surgical access device is provided includes a seal having an opening configured to receive a surgical instrument therethrough and an absorbent element associated with the seal and configured to absorb fluid away from at least one of the opening and a surgical instrument passed through the opening. While the absorbent element can have various configurations, in one exemplary embodiment the absorbent element is positioned adjacent to the opening such that it is configured to contact and absorb fluid away from a surgical instrument passed through the opening in the seal, while in other embodiments the absorbent element can be formed integrally with the seal. The absorbent element can be formed of any material known in the art including, but not limited to a polyester, such as polyethylene terephthalate (PET), spunbond polyethylene terephthalate, nylon polyester, rayon, cellulose acetate, polyolefin, a foam, such as a polyurethane foam, cotton, and combinations thereof. The seal can include at least one of an instrument seal configured to form a seal around a surgical instrument disposed therethrough and a zero-closure seal configured to form a seal when no surgical instrument is disposed therethrough. In one embodiment, the seal can be configured to scrape fluid off of a surgical instrument passed through the opening, and the absorbent element can be configured to absorb fluid scraped off of the surgical instrument by the seal. The opening can extend between proximal and distal surfaces of the seal, and the absorbent element can be positioned adjacent to one of the proximal and distal surfaces of the seal.

In other embodiments, the seal assembly can include a scraper element positioned adjacent to the absorbent element and configured to scrape fluid off of a surgical instrument passed through the opening in the seal. The scraper element can include an opening formed therethrough and configured to circumferentially scrape fluid off of a surgical instrument passed therethrough. The scraper element can have various configurations, but in one embodiment the scraper element can be a cone-shaped scraper extending distally from a distal surface of the seal and having an opening for receiving and scraping a surgical instrument. The absorbent element can be substantially cone-shaped and the cone-shaped scraper can be nested within the substantially cone-shaped absorbent element. In another exemplary embodiment, the scraper element can be a disc having an opening for receiving and scraping a surgical instrument and the absorbent element can be positioned adjacent to the disc and configured to absorb fluid scraped by the disc.

The seal can have various configurations, but in one embodiment the seal includes a flexible member and a multi-layer protective member. The absorbent element can be positioned between layers of the multi-layer protective member. The absorbent element can also be a multiple layer absorbent element. In another embodiment, the seal can be a zero-closure seal and the absorbent element can include at least two absorbent flapper doors positioned adjacent to a distal surface of the zero-closure seal. In other aspects, the seal can be a zero-closure seal having a first member nested within a second member, and the absorbent element can be positioned between the first and second members of the zero-closure seal and configured to absorb fluids as the zero-closure seal opens and closes. In still a further embodiment, the absorbent element can include at least two absorbent bars configured to contact and absorb fluid away from a surgical instrument passed through the opening in the seal and between the at least two absorbent bars. In other aspects, the absorbent element can include a plurality of absorbent elements and the seal assembly can further include a plurality of scrapers in communication with the plurality of absorbent elements. The plurality of scrapers can be configured to scrape fluid from a surgical instrument passed through the opening in the seal.

In another embodiment, a surgical access device is provided and can include a housing defining a working channel sized and configured to receive a surgical instrument. A seal can be disposed within the housing and it can have an opening positioned to receive a surgical instrument passed through the working channel. An absorbent element can be disposed in the housing and configured to absorb fluid to prevent fluid from being re-deposited on surgical instruments passed through the working channel.

While the absorbent element can have various configurations, in one exemplary embodiment the absorbent element is positioned to absorb fluid off of a surgical instrument passed through the housing. The absorbent element can also be positioned to absorb fluid away from the opening in the seal and/or can be formed integrally with the seal. In certain exemplary embodiment, the surgical access device can be a trocar and the housing can include a proximal portion containing the seal and a distal cannula extending distally from the proximal portion and configured to be inserted into a body cavity.

In another exemplary embodiment, the surgical access device can include a scraper disposed in the housing and configured to scrape fluid off of a surgical instrument passed through working channel. The absorbent element can be configured to absorb fluid scraped by the scraper. In one embodiment, the scraper can be substantially cone-shaped and can have an opening for receiving and scraping a surgical instrument. The absorbent element can be substantially cone-shaped and the scraper can be nested within the absorbent element so that the absorbent element is configured to absorb fluids scraped by the scraper.

In other embodiments, the scraper can include a disc having an opening for receiving and scraping a surgical instrument and the absorbent can be positioned adjacent to the opening in the disc. The absorbent can include a plurality of absorbents, and the surgical access device can further include a plurality of scrapers in communication with the plurality of absorbents and configured to scrape fluid from a surgical instrument passed through the working channel. In one embodiment, the seal can include a multi-layer flexible member and the absorbent can be positioned between layers of the multi-layer protective member. The absorbent and the seal can be positioned in contact with one another and they can have substantially the same shape.

Methods for removing fluid from a seal opening are also provided and can include passing a surgical instrument through an opening in a seal in an access device, wherein fluid on the instrument is absorbed by an absorbent element in the access device. The absorbent element can absorb fluid away from the instrument and can absorb fluid deposited on the seal by the instrument. A scraper element can be disposed in the access device and can scrape fluid from the surgical instrument as it is passed through the access device and the absorbent element can absorb fluid scraped by the scraper. In one embodiment, the absorbent element can absorb fluid as the seal opens and closes. In another embodiment, the access device can include a trocar and the method can further include inserting a trocar through tissue to form a working channel extending into a body cavity.

In other embodiments, a seal assembly is provided for use in a surgical access device and can include at least one seal configured to receive a surgical instrument therethrough. The at least one seal can be configured to form a seal around a surgical instrument disposed through the opening and to form a seal when no surgical instrument is disposed therethrough. The seal assembly can further include a scraper adjacent to the seal and configured to scrape fluid off of a surgical instrument extending through the opening in the seal. In one embodiment, the scraper can be positioned a distance apart from the seal.

While the at least one seal can have various configurations, in one aspect the at least one seal can include a single seal element that is configured to both form a seal around a surgical instrument disposed through the opening and to form a seal when no surgical instrument is disposed therethrough. In another embodiment, the seal can include an instrument seal having an opening formed therethrough and configured to form a seal around a surgical instrument disposed therethrough, and a zero-closure seal configured to form a seal when no surgical instrument is disposed therethrough. While the scraper can have various configurations, in some embodiments, the scraper can be positioned between the instrument seal and the zero-closure seal.

The scraper can have various configurations. For example, the scraper can include first and second rotatable members configured to rotate as a surgical instrument is passed therethrough. In another embodiment, the seal can be substantially conical shaped and can include a protector disposed proximal to the seal, and the scraper can be disposed distal to the seal. The protector and seal can each include multiple layers. In one exemplary embodiment, the scraper can be substantially cone shaped. The scraper can also include at least one slit formed therein and configured to allow the scraper to radially expand. An inner portion of the scraper can include a fluid collection member configured to collect fluid scraped by the scraper. The fluid collection member can include a substantially C-shaped lip and at least a portion of the fluid collection member can be absorbent. In some embodiments, at least a portion of the scraper can be adapted to absorb fluid.

In another embodiment, a surgical access device is provided having a housing defining a working channel sized and configured to receive a surgical instrument. A seal assembly can be disposed in the housing for forming a seal around a surgical instrument disposed through the working channel, and for forming a seal in the working channel when no surgical instrument is disposed through the working channel. A scraping element can be disposed in the housing and positioned to scrape fluid off of a surgical instrument passed through the working channel.

The housing can have various configurations, but in one embodiment the housing can include a proximal portion containing the seal assembly and a distal cannula extending from the proximal portion and configured to be inserted into a body cavity. The seal assembly can also have various configurations. For example, the seal assembly can include a first seal having an opening configured to form a seal around a surgical instrument disposed therethrough, and a second seal configured to form a seal in the working channel of the housing when no instrument is disposed therethrough. In some embodiments, the scraping element can be positioned between the first and second seals. In other embodiments, the scraping element can be positioned distal to the first and second seals. In another embodiment, the seal assembly can include a single seal configured to both form a seal around a surgical instrument disposed through the working channel and to form a seal in the working channel when no surgical instrument is disposed through the working channel.

The scraping element can have a variety of configurations. In one embodiment, the scraping element can be expandable. In another embodiment, the scraping element can include first and second rotatable members configured to rotate as a surgical instrument is passed therethrough. The scraping element can have various shapes and sizes, but in one embodiment the scraping element is substantially cone shaped and at least a portion of the scraping element can be absorbent. The scraping element can be disposed in a removable cap of the housing and/or it can be removably matable to the housing. An inner portion of the scraping element can include a fluid collection member configured to collect fluid scraped by the scraper.

Methods for scraping fluid away from a surgical instrument are also provided and can include passing a surgical instrument through at least one seal in a surgical access device extending into a body cavity such that the seal forms a seal in the surgical access device when no surgical instrument is disposed therethrough and forms a seal around the surgical instrument when the surgical instrument is disposed therethrough. A scraper in the surgical access device can engage the surgical instrument to scrape fluid therefrom to prevent fluid from accumulating on the seal.

The seal can include an instrument seal that forms a seal around the surgical instrument disposed therethrough and a zero-closure seal that forms a seal in the surgical access device when no instrument is disposed therethrough. Alternatively or in addition, the seal can be a single seal that both forms a seal in the surgical access device when no surgical instrument is disposed therethrough and forms a seal around the surgical instrument when the surgical instrument is disposed therethrough.

The method can further include an absorbent that absorbs the fluid that is scraped away from the surgical instrument. In one embodiment, the scraper can expand to engage the surgical instrument. In another embodiment, the scraper can rotate to engage the surgical instrument. A portion of the scraper can optionally absorb the fluid that is scraped away from the surgical instrument and a portion of the scraper can collect the fluid that is scraped away from the surgical instrument.

In another exemplary embodiment, a seal assembly for use in a surgical access device is provided with a seal having an opening configured to receive a surgical instrument therethrough and a wicking element associated with the seal configured to wick away fluid collected near the opening when a surgical instrument is passed through the seal. The opening can extend between proximal and distal surfaces of the seal, and the wicking element can be positioned adjacent to one of the proximal surface and the distal surface of the seal and can be configured to wick away fluid scraped off of a surgical instrument by the seal.

The wicking element can have various configurations. In one embodiment, the wicking element can be formed integrally with the seal. In another embodiment, the wicking element can be positioned such that it is configured to contact and wick away fluid from a surgical instrument passed through the opening in the seal. In other aspects, the seal can have a generally conical configuration with an opening formed therethrough and configured to form a seal around an instrument, and the wicking element can include at least one rib formed on a surface of the seal that can extend outward from the opening for wicking fluid away from the opening.

In another embodiment, the seal can be a zero-closure seal and the wicking element can include at least two wicking fingers extending from the zero-closure seal. The two wicking fingers can be in communication with an absorbent reservoir configured to absorb fluid wicked away from the zero-closure seal by the wicking fingers. The wicking element can also be a multi-layer protective member positioned in proximity to the seal and having an opening with a diameter greater than a diameter of the seal opening to create a gap between the seal opening and the protective member opening for receiving fluid therebetween. In another embodiment, the wicking element can be a multi-layer protective member positioned in proximity to the seal and having surface features formed thereon to create a gap between the seal opening and the protective member opening for receiving fluid therebetween.

In other aspects, the wicking element can have an hourglass shape sized to scrape fluid from a surgical instrument passed through a central opening in the wicking element. In another embodiment, the wicking element can include drainage slots adjacent to the opening for wicking fluid from an interior surface to an exterior surface of the wicking element. In yet another embodiment, the seal can include a flexible member having an opening configured to form a seal around a surgical instrument disposed therethrough and an adjacent multi-layer protective member, and the wicking element can include camming ribs on a surface of at least one of the flexible member and the multi-layer protective member and configured to create a gap between the flexible member and the multi-layer protective member such that fluid is wicked away from the opening in the seal. In still another embodiment, the wicking element can be a plurality of holes disposed in the multi-layer protective member and configured to wick away fluid from the opening in the flexible member.

In another embodiment, a surgical access device is provided having a housing defining a working channel sized and configured to receive a surgical instrument. A seal can be disposed within the housing and can have an opening configured to form a seal around a surgical instrument disposed therethrough. A wicking element can be disposed in the housing and can be configured to wick fluid accumulated around the seal opening. The housing can have various configurations, but in one embodiment the housing can include a proximal portion containing the seal and a distal cannula extending distally from the proximal portion that can be configured to be inserted into a body cavity. The opening in the seal can be formed between at least two sealing walls movable between a sealed closed position and an open position in which the opening receives a surgical instrument.

The wicking element can have various shapes, sizes, and configurations and in one embodiment the wicking element can include at least two extension members formed on the two sealing walls that can be configured to contact an interior wall of the working channel when the sealing walls are in the open position so that fluid disposed on the seal is wicked onto the interior wall of the working channel. In another embodiment, the wicking element can include a plurality of drainage slots formed in the distal cannula and configured to wick fluid from an interior portion of the distal cannula to an exterior surface of the distal cannula. In still another embodiment, the seal can include a zero-closure seal and the wicking element can include at least two wicking fingers extending from the zero-closure seal. The two wicking fingers can be in communication with an absorbent reservoir configured to absorb fluid wicked away from the zero-closure seal by the two wicking fingers. The wicking element can also be a multi-layer protective member positioned in proximity to the seal having an opening with a diameter greater than a diameter of the seal opening to create a gap between the seal opening and the protective member opening for receiving fluid therebetween. In another embodiment, the wicking element can have an hourglass shape sized to scrape fluid from a surgical instrument passed through a central opening in the wicking element. The wicking element can include drainage slots adjacent to the opening for wicking fluid from an interior surface to an exterior surface of the wicking element. In another embodiment, the seal can include a flexible member and multi-layer protective member, and the wicking element can include camming ribs on a surface of at least one of the multi-layer of the protective member and the flexible member and can be configured to create a gap between the flexible member and the multi-layer protective member so that fluid is wicked away from the opening in the seal. The wicking element can also include a plurality of holes disposed in the multi-layer protective member and configured to wick away fluid from the opening in the flexible member.

Methods for removing fluid from a seal opening are also provided and can include passing a surgical instrument through an opening in a seal in a surgical access device defining a working channel extending into a body cavity, wherein fluid on the seal is wicked away from the opening when the instrument is passed through the opening. A wicking element can be disposed in the access device and can wick fluid from the surgical instrument as it is passed through the trocar. The wicking element can also wick away fluid as the seal opens and closes. In one embodiment, an absorbent absorbs the fluid that is wicked away. In another embodiment, a scraper can scrape fluid off of the instrument as the instrument is passed through the opening.

BRIEF DESCRIPTION OF THE DRAWINGS

The invention will be more fully understood from the following detailed description taken in conjunction with the accompanying drawings, in which:

FIG. 6A is a cross-sectional view of a trocar having one embodiment of a scraper for scraping fluid away from a surgical instrument passed therethrough;

FIG. 6B is a cross-sectional view of a trocar having another embodiment of a scraper for scraping fluid away from a surgical instrument passed therethrough;

FIG. 6C is a cross-sectional view of a trocar having yet another embodiment of a scraper for scraping fluid away from a surgical instrument passed therethrough;

DETAILED DESCRIPTION OF THE INVENTION

Figure 1A:
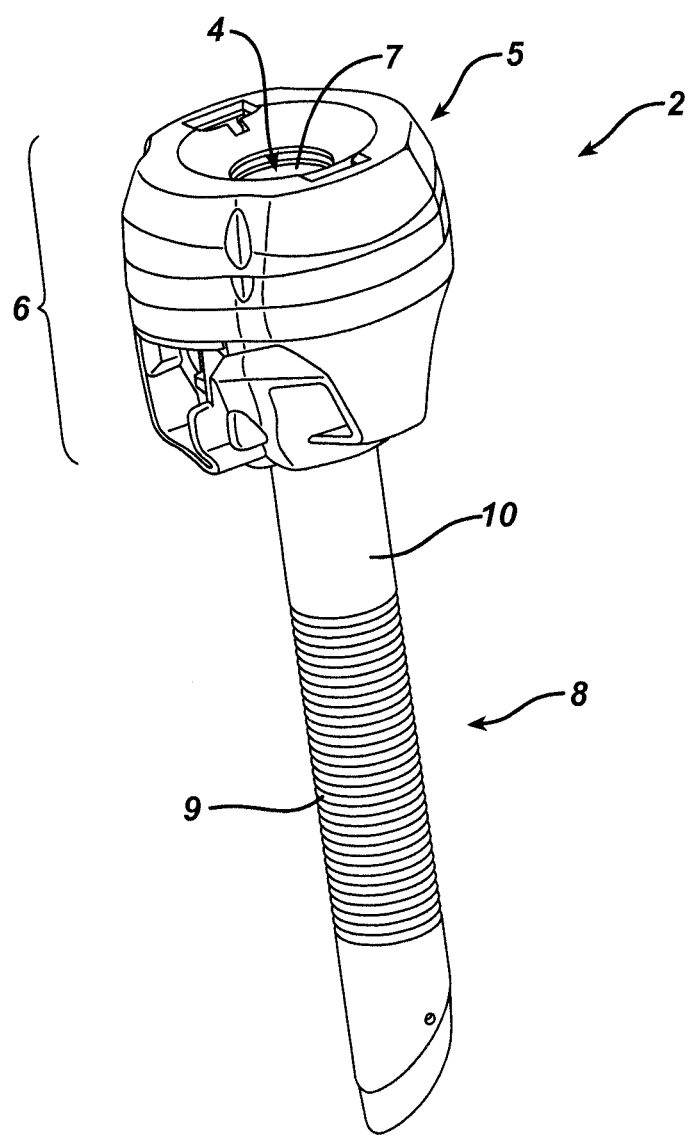
FIG. 1A is a perspective view of one embodiment of a trocar.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for maintaining clear visibility through a scoping device during surgical procedures, and in particular methods and devices are provided for removing fluid from an access device and/or surgical instrument passed, e.g., inserted and/or withdrawn, through an access device, and/or for preventing fluid from being transferred onto a scoping device passed through an access device. In certain exemplary embodiments, the methods and devices are effective to remove fluid from an access device and/or surgical instrument as the instrument is being withdrawn from the access device, thus preventing the fluid from being deposited onto an instrument being inserted through the access device. However, the methods and devices can be configured to remove fluid prior to and/or during insertion and/or removal.

A person skilled in the art will appreciate that the term fluid as used herein is intended to include any substance that, when on a surgical instrument, can adversely affect the functioning of the instrument or a surgeon's ability to use it. Fluids include any kind of bodily fluid, such as blood, and any kind of fluid introduced during a surgical procedure, such as saline. Fluids also include fluid/solid mixtures or fluids with particles (such as pieces of tissue) suspended or located therein, as well as viscous materials and gases. A person skilled in the art will also appreciate that the various concepts disclosed herein can be used with various surgical instruments during various procedures, but in certain exemplary embodiments the present invention is particularly useful during laparoscope procedures, and more particularly during procedures in which a scoping device, such as an laparoscope or endoscope, is passed through a surgical access device, such as a trocar, that provides a pathway from a skin incision to a body cavity. As previously explained, during such procedures repeated insertion and withdrawal of the scoping device can deposit fluid within the access device, thus allowing the fluid to be transferred back onto the distal viewing end of the scoping device upon reinsertion therethrough. Various exemplary methods and devices are provided herein to prevent such an occurrence.

In certain exemplary embodiments, the methods and devices disclosed herein utilize a fluid remover that is effective to remove fluid from an access device and/or surgical instrument passed therethrough. While the fluid remover can have various configurations and it can function in various manners to remove fluid, exemplary fluid removers includes scrapers for scraping fluids, absorbents for absorbing fluid, and wicking elements for redirecting or wicking fluid away, e.g., by capillary action. Any combination of fluid removers can be provided, and the fluid removers can be disposed at various locations within an access device to remove fluid from portions of the access device and/or from surgical instruments, such as scoping devices, passed through the access device. The particular location of the fluid remover(s) can depend on the particular configuration of the access device and/or surgical instrument.

Figure 1B:
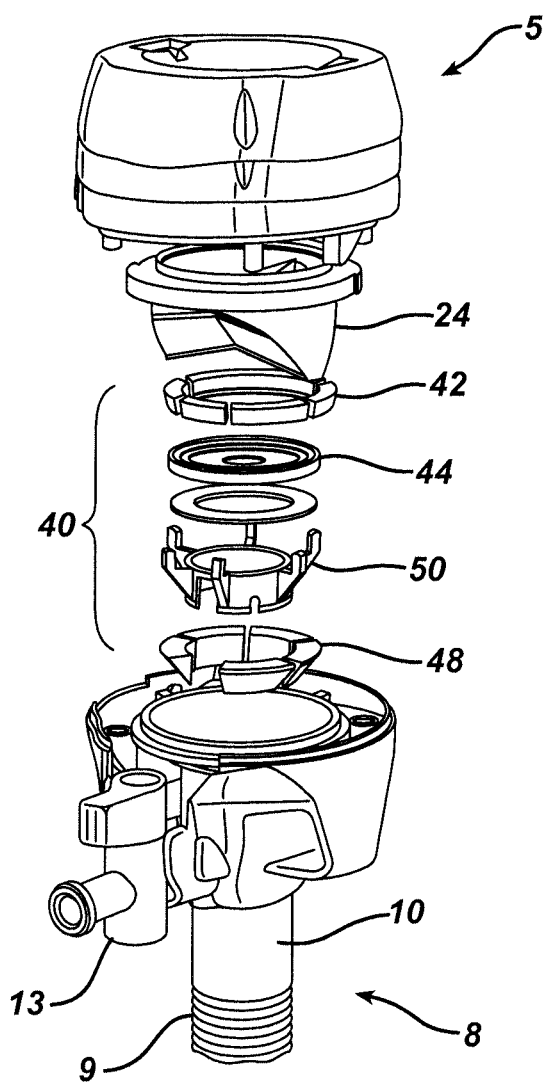
FIG. 1B is an exploded view of the trocar of FIG. 1A.
Figure 1C:
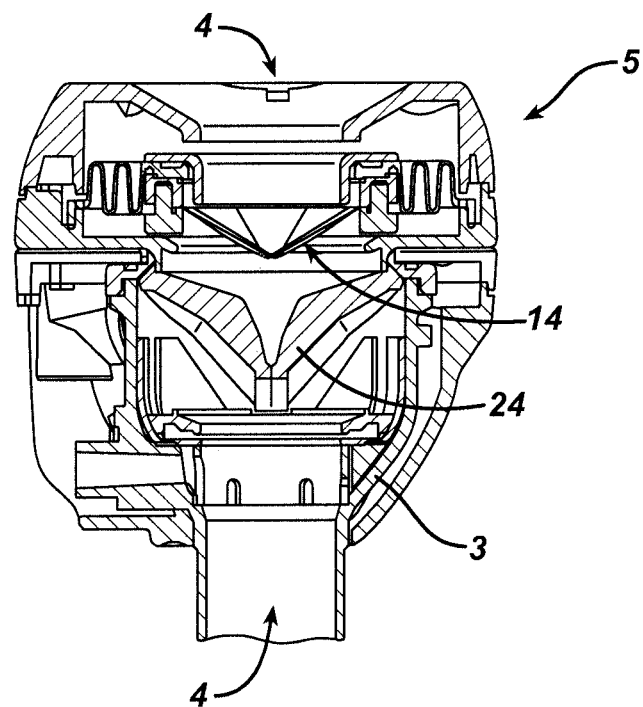
FIG. 1C is a cross-sectional view of a portion of the trocar of FIG. 1A.

While the fluid removers disclosed herein can be used with various surgical access devices known in the art, in certain exemplary embodiments a trocar is provided having one or more fluid removers disposed therein for removing fluid from portions of the trocar and/or from an instrument, such as a scoping device, passed therethrough. A person skilled in the art will appreciate that a trocar is shown for illustration purposes only, and that virtually any type of access device, including cannulas, ports, etc., can be used. FIGS. 1A-1C illustrate one exemplary embodiment of a trocar 2. As shown, the trocar 2 is generally in the form of a housing 6 having a proximal portion (also referred to herein as a proximal housing) that can house one or more sealing elements and a distal cannula 8 extending distally from the proximal housing 6. The trocar 2 defines a working channel 4 extending therethrough for introducing various instruments into a body cavity. A number of configurations are available for the proximal housing 6. In the illustrated embodiment, the proximal housing 6 has a generally cylindrical shape with a removable cap portion 5 and an inner sidewall 3. An opening 7 can be formed in the proximal end of the housing 6, such that the opening 7 extends through the removable cap 5 and through the remainder of the housing 6 and is coaxial with the working channel 4 extending through the cannula 8. The cannula 8 can also have various configurations, and can include various features known in the art. In the illustrated embodiment, the cannula 8 has a generally elongate cylindrical shape and includes a series of annular ridges 9 formed on an external surface 10 thereof. The opening 7 extending through the proximal housing 6 and the cannula 8 define the working channel 4 that is sized and configured to receive a surgical instrument. One skilled in the art will appreciate that the housing 6 and the cannula 8 can be formed as a unitary structure or as two separate components that are mated to one another. The housing 6 can also include other features, such as a stop-cock valve 13 for allowing and preventing the passage of an insufflation fluid, e.g. carbon dioxide, through the trocar 2 and into a body cavity.

In use, the distal cannula 8 can be inserted through a skin incision and through tissue to position a distal-most end within a body cavity. The proximal housing 6 can remain external to the body cavity, and various instruments can be inserted through the working channel 4 and into the body cavity. Typically, during surgical procedures in a body cavity, such as the abdomen, insufflation is provided through the trocar 2 to expand the body cavity to facilitate the surgical procedure. Thus, in order to maintain insufflation within the body cavity, most trocars include at least one seal disposed therein to prevent air from escaping. Various seal configurations are known in the art, but typically the trocar 2 includes an instrument seal that forms a seal around an instrument disposed therethrough, but otherwise does not form a seal when no instrument is disposed therethrough; a trocar seal or zero-closure seal that seals the working channel 4 when no instrument is disposed therethrough; or a combination instrument seal and trocar seal that is effective to both form a seal around an instrument disposed therethrough and to form a seal in the working channel 4 when no instrument is disposed therethrough. In the embodiment shown in FIGS. 1A-1C the trocar 2 includes an instrument seal 14 and a separate trocar or zero-closure seal. However, a person skilled in the art will appreciate that various other seals known in the art can be used including, for example, flapper valves, gel seals, diaphragm seals, etc.

Figure 1D:
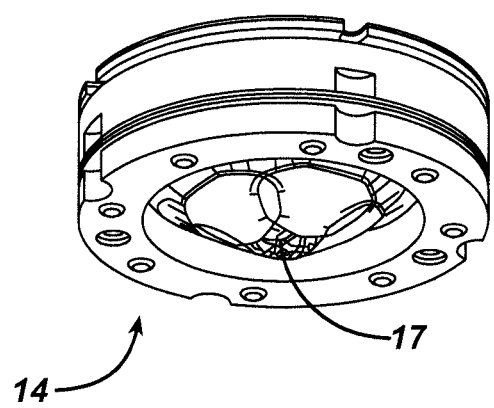
FIG. 1D is a bottom perspective view of an instrument seal assembly for use with the trocar of FIG. 1A.
Figure 1E:
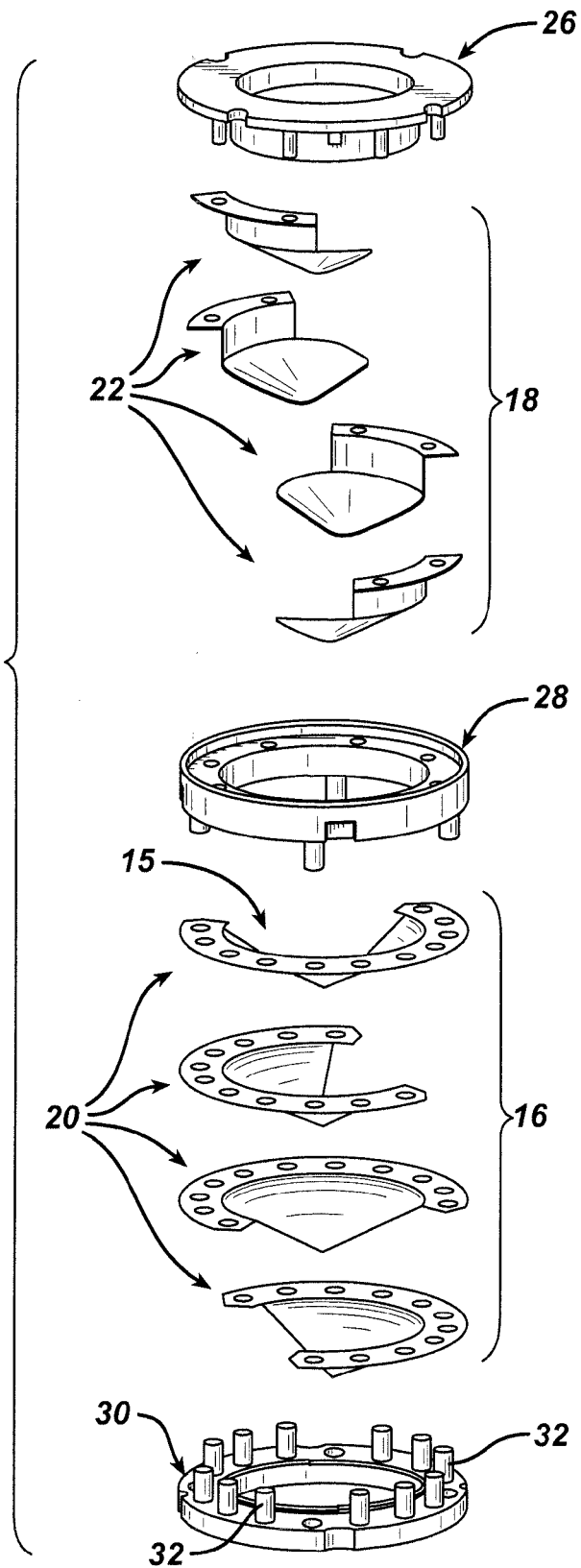
FIG. 1E is an exploded view of the instrument seal assembly of FIG. 1D.

In an exemplary embodiment, as shown in FIGS. 1C-1E, the instrument seal 14 is generally in the form of a multi-layer conical seal 16 and a multi-layer protective member 18 disposed on a proximal surface 15 of the seal 16. As best shown in FIG. 1E, the multi-layer conical seal 16 can include a series of overlapping seal segments 20 that are assembled in a woven arrangement to provide a complete seal body. The seal segments 20 can be stacked on top of one another or woven together in an overlapping fashion to form the multi-layer seal 16 having a central opening 17 therein. The seal segments 20 can be made from any number of materials known to those skilled in the art including, but in an exemplary embodiment the seal segments 20 are formed from an elastomeric material. The seal segments 20 can also be molded such that they have a varying thickness across the profile of the seal 16. Varying the thickness across to the profile of the seal 16 can be effective to minimize leakage and reduce drag forces on the instrument. The multi-layer protective member 18 can similarly be formed from a series of overlapping segments 22 that are disposed proximal to the overlapping seal segments 20 and that are configured to protect the seal segments 20 from damage caused by surgical instruments passed through the opening 17 in the seal 16. The protective member 18 can also be formed from various materials, but in certain exemplary embodiments the protective member 18 is formed from a molded thermoplastic polyurethane elastomer, such as Pellethane™. The segments 20, 22 that form the seal 16 and the protective member 18 can be held together using various techniques known in the art. As shown in FIGS. 1D and 1E, the segments 20, 22 are held together by several ring members that mate to engage the segments 20, 22 therebetween. In particular, the protective member 18 is engaged between a crown 26 and a gasket ring 28, and the seal 16 is engaged between the gasket ring 28 and a retainer ring 30. Pins 32 are used to mate the ring members 26, 28 and to extend through and engage the segments of the seal 16 and protective member 18.

When fully assembled, the instrument seal 14 can be disposed at various locations within the trocar 2. In the illustrated embodiment, the instrument seal 14 is disposed in the cap 5 of the trocar 2 at a location just distal of the proximal opening 7 and proximal of a trocar seal, as discussed in more detail below. In use, an instrument can be passed through the center of the seal assembly and the seal segments 20, 22 can engage and form a seal around an outer surface of the instrument to thereby prevent the passage of fluids through the seal 14. When no instrument is disposed therethrough, the opening will not form a seal in the working channel 4, however other configurations in which a seal is formed when no instrument is disposed therethrough are also conceivable. Exemplary instrument seal configurations are described in more detail in U.S. Publication No. 2004/0230161 entitled "Trocar Seal Assembly," filed on Mar. 31, 2004, and U.S. application Ser. No. 10/687,502 entitled "Conical Trocar Seal," filed on Oct. 15, 2003, which are hereby incorporated by reference in their entireties.

Figure 1F:
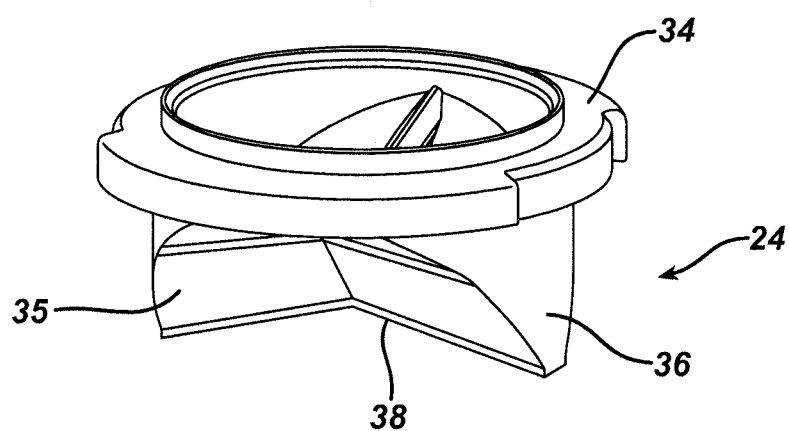
FIG. 1F is a perspective view of a trocar seal of the trocar of FIG. 1A.

The trocar or zero-closure seal in the illustrated embodiment is shown in more detail in FIG. 1F, and as shown the illustrated zero-closure seal is in the form of a duckbill seal 24. The seal 24 is configured to form a seal in the working channel 4 when no instrument is disposed therethrough to thus prevent the leakage of insufflation gases delivered through the trocar 2 to the body cavity. As shown, the duckbill seal 24 has a generally circular flange 34 with a sidewall 36 extending distally therefrom. The shape of the sidewall 36 can vary, but in the illustrated embodiment, the sidewall 36 includes opposed flaps 35 that extend at an angle toward one another in a distal direction and that come together at a distal end to form a seal face 38. The opposed flaps 35 are movable relative to one another to allow the seal face 38 to move between a closed position, in which no instrument is disposed therethrough and the seal face 38 seals the working channel 4 of the trocar 2, and an open position in which an instrument is disposed therethrough. The seal can include various other features, as described in more detail in U.S. application Ser. No. 11/771,263, entitled "Duckbill Seal with Fluid Drainage Feature," filed on Jun. 29, 2007, which is hereby incorporated by reference in its entirety.

In accordance with the present disclosure the general structure of the seals as well as the trocar do not generally form part of the present invention. As such, a person skilled in the art will certainly appreciate that various seal configurations, as well as various trocars, can be used without departing from the spirit of the invention disclosed herein.

As indicated above, a fluid remover can be disposed within the trocar 2 to remove fluid from a seal and/or from a surgical instrument extending through the seal. As best shown in FIGS. 1B-1C, the illustrated trocar 2 includes a fluid remover assembly 40 that is disposed within the proximal housing 6 of the trocar 2 at a location distal of the duckbill seal 24. The fluid removal assembly 40 includes a scraper for scraping fluid off of a surgical instrument passed through the working channel 4 in the trocar 2, and an absorbent for absorbing removed fluid. The scraper can also include a wicking feature for wicking fluid away from the opening in the scraper, and/or the absorbent can include a wicking feature for wicking fluid away from the scraper.

Figure 1G:
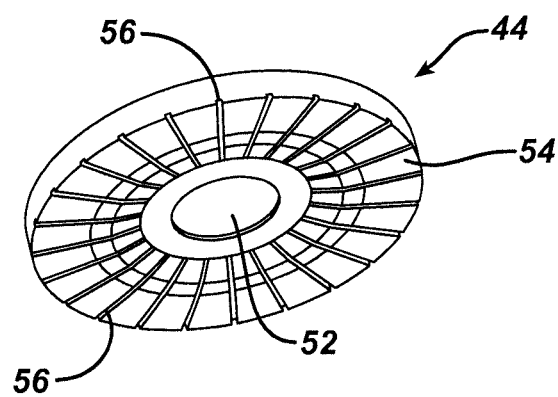
FIG. 1G is a bottom perspective view of one embodiment of a scraper of a fluid remover assembly for use with the trocar of FIG. 1A.
Figure 1H:
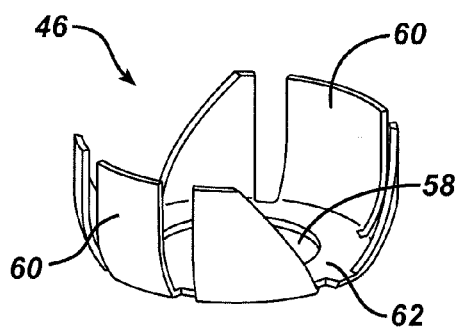
FIG. 1H is a perspective view of one embodiment of an absorbent wick of a fluid remover assembly for use with the trocar of FIG. 1A.
Figure 1I:
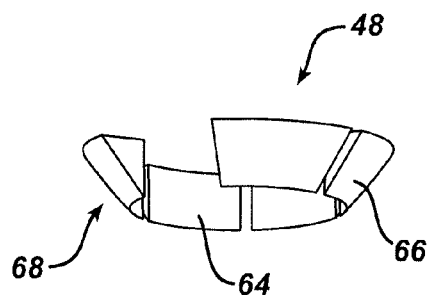
FIG. 1I is a perspective view of an absorbent element of a fluid remover assembly for use with the trocar of FIG. 1A.
Figure 1J:
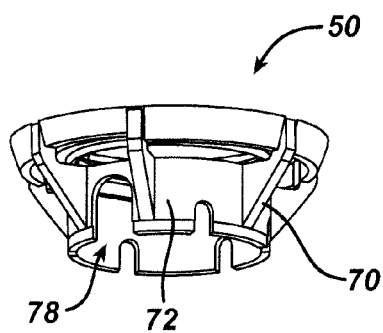
FIG. 1J is a perspective view of a frame for housing the absorbent element of FIG. 1I.
Figure 1K:
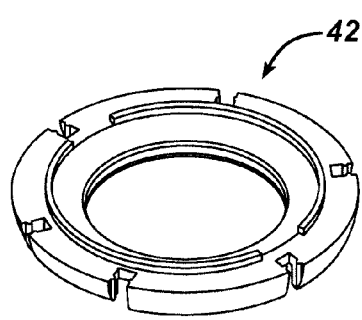
FIG. 1K is a perspective view of a lid portion of a fluid remover assembly for use with the trocar of FIG. 1A.

The components of the fluid remover assembly 40 are shown in more detail in FIGS. 1G-1K, and as shown the assembly generally includes a lid 42 (FIG. 1K), a scraper 44 (FIG. 1G), an absorbent wick 46 (FIG. 1H), absorbent cartridges 48 (FIGS. 1I), and a housing or frame 50 (FIG. 1J). When fully assembled, the fluid remover assembly 40 is configured to scrape fluid off of surgical instruments passing through the working channel 4 of the trocar 2, to wick the scraped fluids away, and to absorb them, thereby preventing the fluids from being redeposited on the instrument upon reinsertion through the working channel.

Referring first to FIG. 1G, the scraper 44 can have a variety of configurations, but in an exemplary embodiment, as shown, the scraper has a generally planar configuration with a circular shape. A central opening 52 is formed through a central portion thereof and is sized and configured to receive a surgical instrument therethrough. In use, the central opening 52 can be coaxial with openings in the instrument and trocar seals. The scraper 44 can be formed from various materials, but in an exemplary embodiment the scraper is formed from silicone to allow the scraper 44 to engage and scrape fluid off of any instrument passed therethrough. As further shown in FIG. 1G, a distal-facing surface 54 of the scraper 44 can include a plurality of channels 56 formed therein and extending radially outward from the central opening 52, or from a location just radially outward but adjacent to the central opening 52. The channels 56 can be configured such that fluid scraped off of an instrument by the central opening 52 will flow into the channels 56 and thereby be wicked away from the opening 52.

As indicated above, the fluid remover assembly 40 can also include an absorbent wick 46. As shown in FIG. 1H, in an exemplary embodiment the absorbent wick 46 has a generally planar circular portion 62 with a central opening 58 formed therethrough. The central opening 58 can have a diameter slightly larger than a diameter of the central opening 52 in the scraper 44, and it can be configured to be positioned coaxial with the opening 52 in the scraper 44. As further shown in FIG. 1H, the absorbent wick 46 can also include one or more sidewalls 60 extending from the planar circular portion 62. The illustrated sidewalls 60 extend proximally, however they can extend distally depending on the particular configuration of the wick 46. The sidewalls 60 can be configured to sit within the inner sidewall 3 of the trocar housing 6. In use, the absorbent wick 46 can wick and absorb fluid away from the central opening 52 in the scraper 44, and it can deliver the fluid to the absorbent cartridges 48, as discussed in more detail below. The absorbent wick 46, as well as various other absorbent members disclosed herein, can be formed from a variety of absorbent materials. Exemplary materials include, by way of non-limiting example, hydrophilic non-wovens, cellulose, sodium polycrylate, cotton, polyethylene terephthalate, polyethylene, and polypropylene.

The absorbent cartridges 48 are shown in more detail in FIG. 1I, and as shown the cartridges 48 each have a generally semi-circular shape with a width, as measured from an internal surface 64 to an external surface 66, that decreases in a proximal to distal direction to form wedge-shaped members 68. Together, the cartridges 48 can have an annular configuration. In use, the cartridges 48 can absorb fluid from the absorbent wick 46, thereby storing the fluid at a location away from any instrument passed through the working channel 4. The cartridges 48 can be contained within the trocar 2 by a housing or frame 50, as shown in FIG. 1J. The frame 50 can have a generally cylindrical configuration with an opening 78 extending therethrough, and a plurality of ridges 70 protruding radially outward and extending axially along an outer surface 72 thereof. Each absorbent cartridge 48 can be seated between two ridges.

When fully assembly, the scraper 44 can be seated within the absorbent wick 46, which can rest on top of the frame 50 that holds the absorbent cartridges 48. The lid 42, shown in FIG. 1K, can be seated on top of the scraper 44 and within the absorbent wick 46, and the lid 42 can lock onto the frame 50, thereby holding the fluid remover assembly 40 together. Referring to FIG. 1C, the entire assembly 40 can be seated within the proximal housing 6 of the trocar 2 just distal of the duckbill seal 24. As a result, when an instrument, such as a scoping device, is passed through the working channel 4 of the trocar 2, any fluid on the instrument will be scraped off of the sidewalls of the instrument by the scraper 44. The fluid will flow through the channels 56 and/or be wicked away from the opening 52 by the absorbent wick 46, which delivers the fluid to the absorbent cartridges 48. As a result, when the instrument is withdrawn, for example, the fluid will be prevented from being deposited onto the duckbill seal 24, thereby preventing the fluid from being transferred from the duckbill seal 24 back onto the instrument upon reinsertion.

Figure 2A:
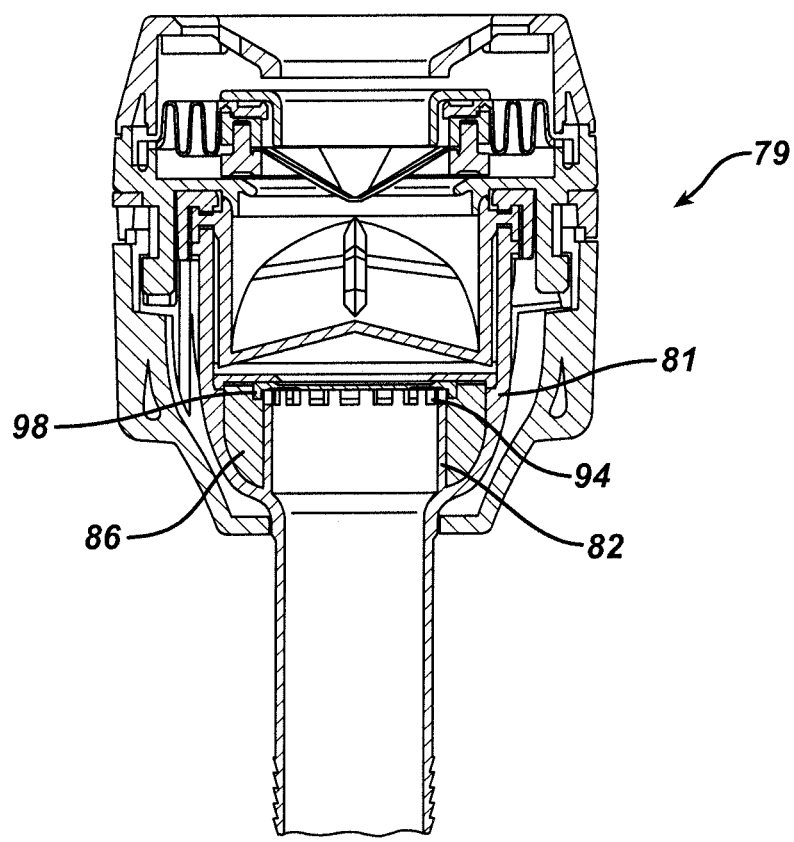
FIG. 2A is a cross-sectional view of a proximal portion of another embodiment of a trocar.
Figure 2B:
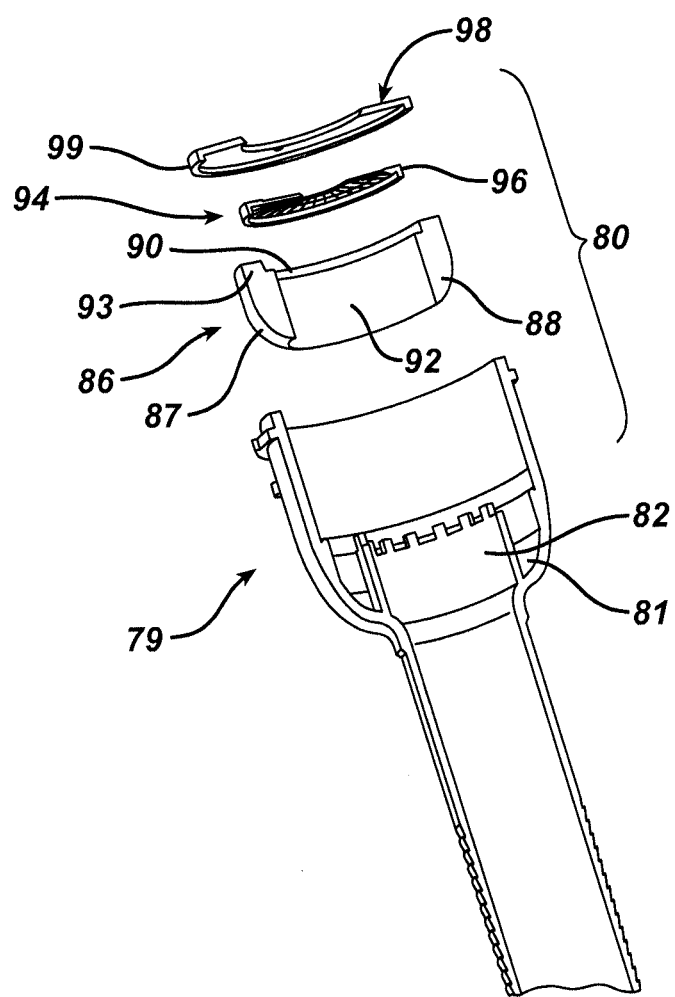
FIG. 2B is an exploded view of the trocar of FIG. 2A.

FIGS. 2A-2B illustrate yet another embodiment of a fluid remover assembly 80 that is similar to the embodiment shown in FIG. 1A. In this embodiment, the proximal housing 79 of the trocar has a frame 82 that is molded into the inner sidewall 81 of the housing 79 for directly seating an absorbent, a scraper, and a lid, thereby eliminating the need for the frame 50 of FIG. 1J. A single absorbent element 86 is also provided, rather than an absorbent wick and separate absorbent cartridges. In particular, the absorbent element 86 in this embodiment has a generally cylindrical configuration with a distal portion 88 that tapers inward on an outer surface 87 thereof to conform to the inner surface 81 of the proximal housing 79 of the trocar. A recess 90 can be formed around an inner surface 92 of a proximal end 93 of the absorbent element 86 to seat a scraper 94, which can have a configuration that is the same as or similar to the scraper 44 described above with respect to FIG. 1G. The recess 90 can engage an outer perimeter 96 of the scraper 94 such that the channels 56 on the scraper 94 can deliver fluid away from the opening 52 in the scraper 94 to the absorbent element 86 surrounding the scraper 94. A cap 98 can sit on top of the scraper 94 and can include a flange 99 that extends around the proximal end 93 of the absorbent element 86. The cap 98 can engage the inner sidewall 81 of the proximal housing 79 of the trocar to retain the scraper 94 and absorbent element 86 therein at a location just distal of the duckbill seal 24. In use, instruments passed through the working channel 4 of the trocar will be engaged by the scraper 94, which scrapes fluid off of the outer surface of the instrument. The fluid is wicked away from the opening 52 in the scraper 94 by the channels 56, which deliver the fluid to the absorbent element 86 surrounding the scraper 94. Thus, similar to the embodiment of FIG. 1A, when the instrument is withdrawn, for example, the fluid will be prevented from being deposited onto the duckbill seal 24, thereby preventing the fluid from being transferred from the duckbill seal 24 back onto the instrument upon reinsertion.

A person skilled in the art will appreciate that the fluid remover assemblies 40, 80 can have a variety of other configurations. FIGS. 3A-10B illustrate additional exemplary embodiments of fluid removers, e.g., scrapers, absorbents, and wicking elements, or combinations thereof. In these embodiments, the fluid removers are all located distal of the duckbill or other zero-closure seal, however a person skilled in the art will appreciate that the particular location of the fluid remover can vary and the fluid removers can be positioned anywhere within the trocar.

Figure 3A:
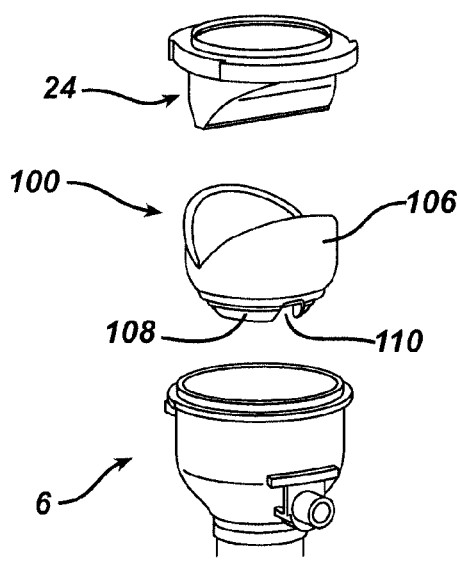
FIG. 3A is an exploded view of a portion of a trocar having a drop-in fluid remover assembly.
Figure 3B:
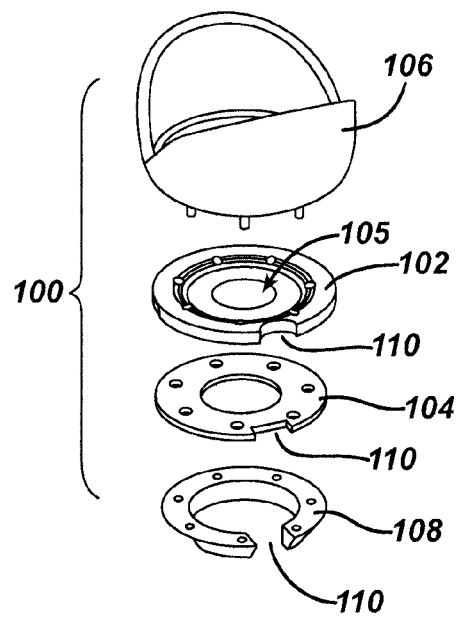
FIG. 3B is an exploded view of the drop-in fluid remover assembly of FIG. 3A.
Figure 3C:
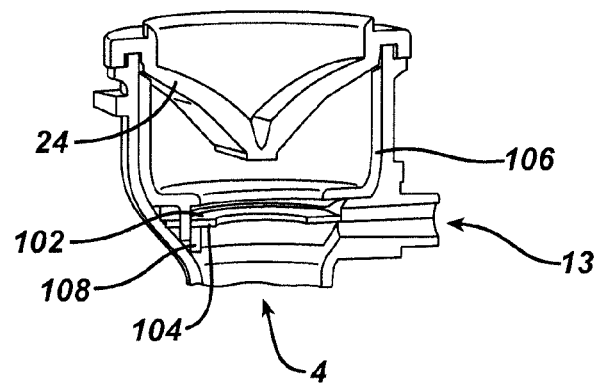
FIG. 3C is a cross-sectional view of a trocar of FIG. 3A.

FIGS. 3A-3C illustrate one embodiment of a fluid remover assembly 100 having a scraper and an absorbent. In particular, as best shown in FIG. 3B, the fluid remover assembly 100 can include a stabilization cup 106 coupled to a flange 108. The stabilization cup 106 can be formed from an absorbent material and the flange 108 can seat the cup 106 within the proximal housing 6 of the trocar 2, as shown in FIG. 3C. A scraper element in the form of a scraper disc 102 can be positioned between the flange 108 and the stabilization cup 106, and an absorbent ring 104 can be coupled to a distal surface of the scraper disc 102. The scraper disc 102 can have a central opening 105 extending therethrough and configured for scraping fluid off of surgical instruments passed through the working channel 4 of the trocar 2. As an instrument is passed through the working channel 4, fluid can be scraped by the scraper disc 102 and absorbed by the absorbent ring, as well as by the stabilization cup. As can be seen in FIG. 3B, the flange 108, scraper disc 102, and absorbent ring 104 can each optionally include cut-outs 110 to fit around the stop-cock 13 associated with the trocar 2. In use, the fluid remover assembly 100 can be formed as a drop-in unit that fits within the proximal housing 6 of the trocar 2. As shown in FIG. 3C, the assembly 100 can be seated in a distal portion of the proximal housing 6 at a location just distal of the duckbill seal 24. The fluid remover assembly 100 will thus remove fluid from instruments passed through the working channel 4 of the trocar, thereby preventing fluid from being deposited onto the duckbill seal and/or redeposited onto instruments passed through the working channel 4.

Figure 4A:
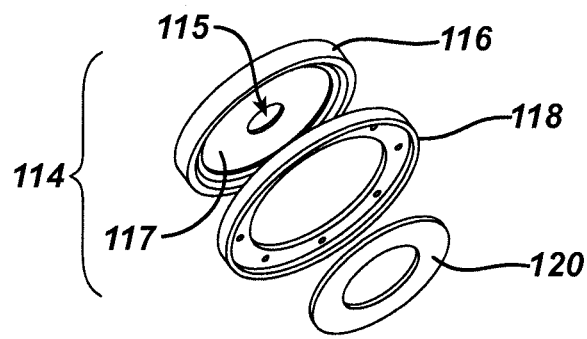
FIG. 4A is an exploded view of one embodiment of a scraper assembly for scraping fluid.
Figure 4B:
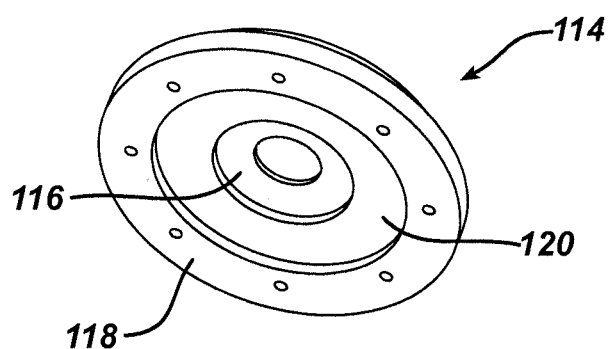
FIG. 4B is a bottom perspective view the scraper assembly of FIG. 4A.
Figure 4C:
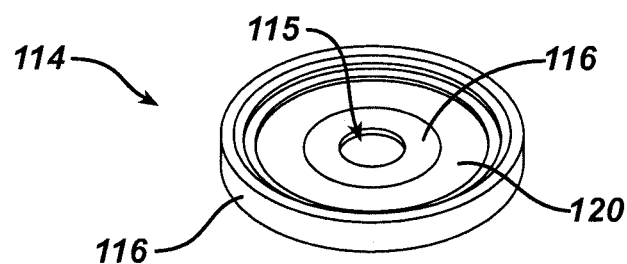
FIG. 4C is a top perspective view of the scraper assembly of FIG. 4A.

FIGS. 4A-4C illustrate another embodiment of a fluid remover assembly 114 that is similar to the assembly shown in FIGS. 3A-3C, however in this embodiment the assembly 114 does not include a stabilization cup. As shown, the fluid remover assembly includes a substantially planar circular scraper disc 116 having a central opening 115 for receiving a surgical instrument. The scraper disc 116 can be seated within a flange or retainer ring 118 configured to be positioned within the proximal housing of a trocar. An absorbent ring 120 can be positioned adjacent to a distal surface 117 of the scraper disc 116 and it can act to absorb any fluid that is scraped off of instruments passed through the scraper disc 116. When disposed within a trocar, the flange 118 can act as a support structure to hold the scraper disc 116 and the absorbent ring 120 in a fixed position within the proximal housing. While the position can be distal to the duckbill seal, as indicated above the assembly can be located at various other portions within the trocar, including between the duckbill seal and the instrument seal, proximal to the instrument seal, or within any portion of the cannula.

Figure 5A:
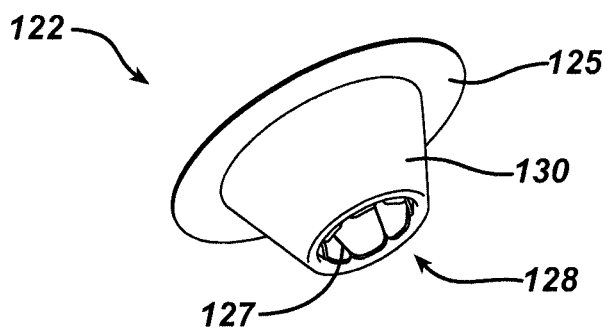
FIG. 5A is a perspective view of another embodiment of fluid remover assembly having a scraper nested within an absorbent element.
Figure 5B:
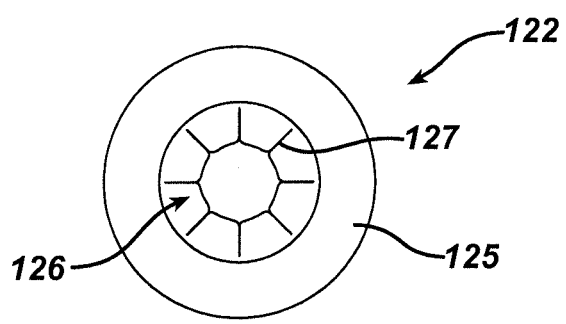
FIG. 5B is top view of the fluid remover assembly of FIG. 5A.
Figure 5C:
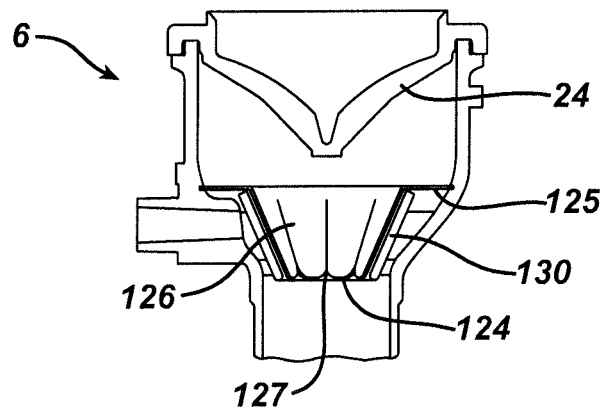
FIG. 5C is a cross-sectional view of the fluid remover assembly of FIG. 5A disposed within a trocar housing.

In another embodiment, shown in FIGS. 5A-5C, a fluid remover assembly 122 is provided and can have a generally conical configuration with a scraper 124 having a proximal generally planar flange 125 and a conical body 126 extending distally therefrom and defining a central opening 128. The conical body 126 can have a plurality of slits 127 extending proximally from a distal end thereof and designed to reduce insertion and withdrawal forces on a surgical instrument passed therethrough. The conical body 126 can be surrounded by a conical absorbent element 130 such that the conical body 126 is nested within the conical absorbent element 130. When assembled and disposed within a trocar, as shown in FIG. 5C, the flange 125 can be seated within the proximal housing 6 just below the duckbill seal 24 and it can mate to or engage the inner sidewall of the housing 6 to retain the fluid remover assembly therein. In use, as an instrument is passed through the working channel, the scraper 124 can engage and scrap fluid off of the instrument and the absorbent element 130 can absorb the fluid. A person skilled in the art will appreciate that any number of geometries can be used in a similar way. Also, a size or diameter of a flange can be adjusted as needed, or the flange can be removed, to seat the fluid remover assembly at other locations within the trocar.

FIGS. 6A-6C illustrate additional embodiments of conical scrapers 132a, 132b, 132c that are similar to the scraper 124 described above and shown in FIGS. 5A-5C. As with the previous embodiment, the scrapers 132a, 132b, 132c in FIGS. 6A-6C are positioned distal to the duckbill seal 24. Such a configuration can prevent fluid on instruments being inserted and/or withdrawn from being deposited on the duckbill seal, as well as the more-proximally located instrument seal 14. In an exemplary embodiment, each scraper 132a, 132b, 132c can be made from a pliable material and can include at least one slit formed therein and configured to allow the scrapers 132a, 132b, 132c to radially expand. A variety of configurations are available for the slit(s). In the embodiment shown in FIG. 6A, a single slit 134 extends diagonally around the scraper 132a such that the slit 134 follows the shape of the cone. In another embodiment shown in FIG. 6B, multiple slits 137 extend proximally from the distal end of the cone and terminate at a location 139 just distal to the proximal end. Such a configuration can yield a scraper having multiple scraping segments 138. As further shown in FIG. 6B, each scraping segment 138 can also include a notch or cut-out 140 formed in an outer surface at the distal end thereof to allow the segment 138 to expand and contact as instruments are passed therethrough. FIG. 6C illustrates another exemplary embodiment of a cone shaped scraper 132c. Similar to the scraper 132b shown in FIG. 6B, the scraper 132c includes several slits 142 that extend proximally from the distal end thereof. In this embodiment, however, the slits 142 increase in width in a distal to proximal direction such that each scraping segment 143 has a distal end 144 with a width that is greater than a width of a proximal end 145 thereof. As indicated above, in use the slit(s) 134, 137, 142 formed in the scrapers 132a, 132b, 132c allow the scrapers to radially expand as a surgical instrument is passed therethrough, thus accommodating instruments of various sizes while still being effective to scrape fluid off of the instruments.

Figure 7:
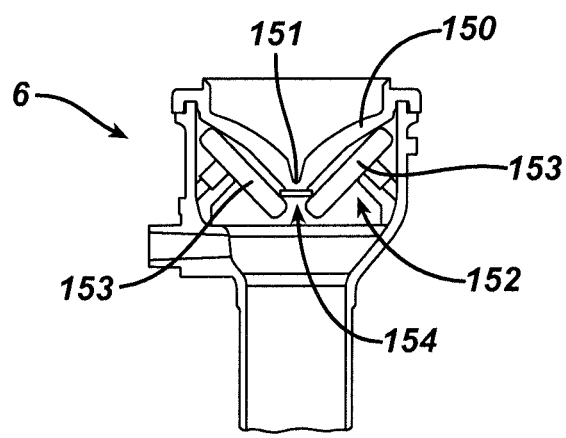
FIG. 7 is a cross-sectional view of another embodiment of a trocar housing having absorbent flapper doors positioned adjacent to a zero-closure seal.

FIG. 7 illustrates another embodiment of a fluid remover positioned just distal of a zero-closure seal or duckbill seal 150 in a proximal housing of a trocar. In this embodiment, the fluid remover is in the form of absorbent flapper doors 152. The flapper doors 152 can have various shapes and sizes, and they can be formed from any number of components. For example, the flapper doors 152 can be in the form of two sidewalls 153 that are movable relative to one another. The sidewalls 153 can have a profile that is similar to the profile of the duckbill seal 150. In other embodiments, the flapper doors 152 can have a shape that corresponds to the shape of the duckbill seal 150. A person skilled in the art will appreciate that various configurations are possible. The flapper doors 152 can be seated inside the proximal housing 6 and attached to the housing 6 by any attachment means known in the art, including by mechanical means, adhesives, etc. The flapper doors 152 can define an opening 154 therebetween for receiving a surgical instrument, and the opening 154 can be positioned just distal of the seal face 151. In use, the flapper doors 152 can move from a closed or substantially closed position to an open position as an instrument is passed through the duckbill seal 150 and the flappers door 152. The doors 152 can contact and engage the surgical instrument as it is being passed therethrough to absorb fluids off of the instrument. The flapper doors 152 can also absorb any excess fluid that is scraped off of the instrument by the duckbill seal 150 and that falls distally from the duckbill seal 150.

Figure 8:
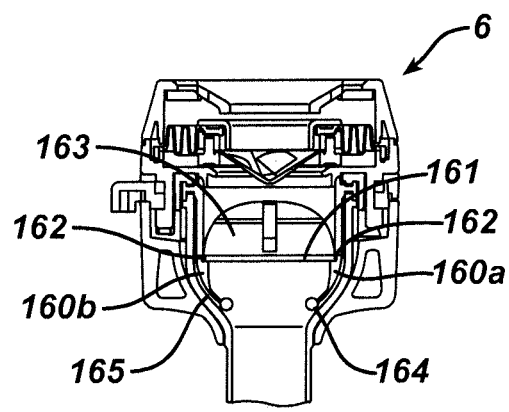
FIG. 8 is a cross-sectional view of yet another embodiment of a trocar housing having wicking fingers coupled to an absorbent reservoir.

In a similar embodiment, shown in FIG. 8, the fluid remover can be in the form of a wicking element rather than an absorbent. In the illustrated embodiment, the wicking element is in the form of first and second wicking fingers 160a, 160b that are coupled to opposed outer edges 162 of the seal face 161 on the duckbill seal 163. The wicking fingers 160a, 160b can be in the form of elongate members that follow the natural shape of the inner sidewall 165 of the proximal housing 6 of the trocar 2 so that fluid will run naturally down the fingers 160a, 160b. The wicking fingers 160a, 160b can also include an absorbent reservoir 164 disposed on a distal end thereof. In the illustrated embodiment, the absorbent reservoir 164 on each finger 160a, 160b is in the shape of ring seated within the proximal housing 6 and effective to absorb the fluids wicked away from the duckbill seal 163 by the wicking fingers 160a, 160b. The absorbent reservoir 164 can, however, have various other configurations such as ring segments. In use, as fluids are deposited on the duckbill seal 163 by instruments passing therethrough, the fluid will naturally flow to outer corners or edges of the seal face 161. The surface difference between the wicking fingers 160a, 160b and the duckbill seal 24 will cause fluid to flow from the seal 163 to the fingers 160a, 160b and down the fingers 160a, 160b into the absorbent reservoir 164. As will be appreciated by those skilled in the art, the wicking fingers 160a, 160b can be formed integrally with the duckbill seal 163 or can simply be in close contact with sealing face 161 of the duckbill seal 163.

Figure 9:
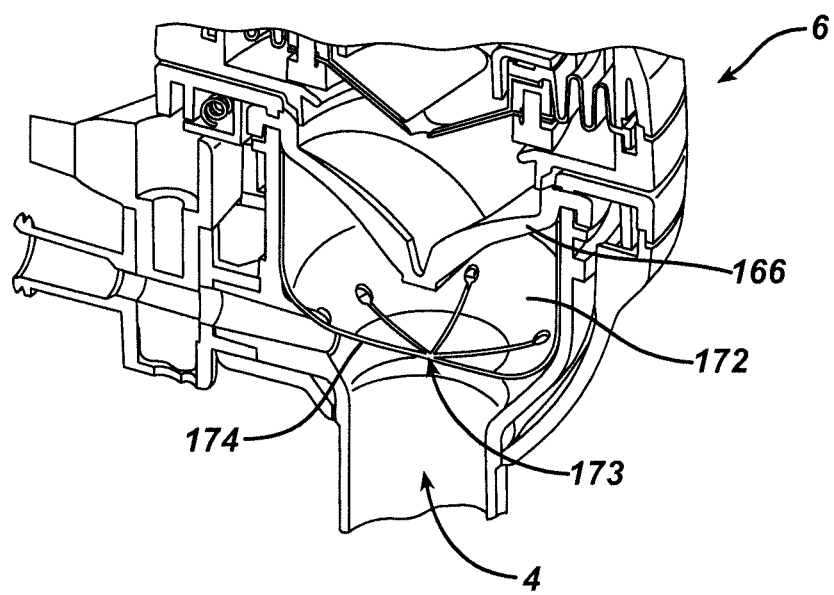
FIG. 9 is a cross-sectional view of one embodiment of a trocar housing having an absorbent element disposed therein.

FIG. 9 illustrates another embodiment of a fluid remover that is positioned distal of a zero-closure seal. Similar to the embodiment shown in FIG. 7, the fluid remover is in the form of an absorbent. However, in this embodiment the absorbent is an absorbent grommet 172. The grommet 172 can have a generally circular or conical configuration with an opening 173 formed therethrough, as shown, but it can have any number of other geometries to facilitate passage of an instrument therethrough. The grommet 172 can also include multiple slits 174 formed therein and extending radially outward from the opening 173 to reduce insertion and withdrawal forces on an instrument being passed therethrough. In use, the grommet 172 can be seated within a distal portion of the proximal housing 6 of the trocar, just distal of the duckbill seal 166, and the opening 173 can be positioned coaxial with the working channel 4. As a surgical instrument is passed therethrough, the grommet 172 will contact the instrument and absorb any fluid on the instrument. The grommet 172 can also absorb any fluid that drips off of the duckbill seal 166 as the seal 166 scrapes the instrument.

Figure 10A:
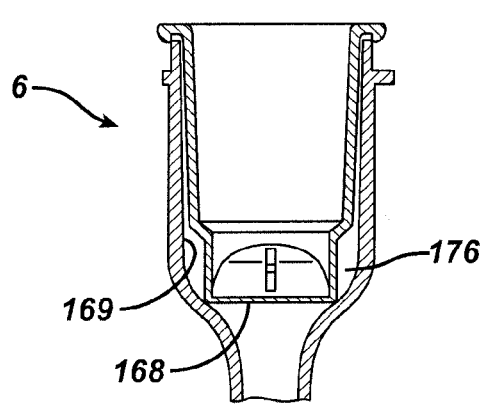
FIG. 10A is a cross-sectional view of one embodiment of a zero-closure seal having extension members for wicking fluid.
Figure 10B:
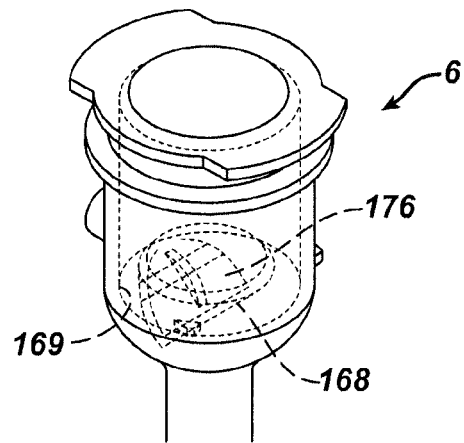
FIG. 10B is a transparent perspective view of the seal of FIG. 10A.

In other embodiments, the zero-closure seal itself can be modified to include a fluid remover. For example, FIGS. 10A and 10B illustrate another embodiment of a duckbill seal 176 in which the seal face 168 is extended distally and expanded in width to cause the outer ends of the seal face 168 to contact the inner sidewall 169 of the proximal housing 6 of the trocar, thereby forming a wicking element. In use, when an instrument is passed through the duckbill seal 176, the seal face 168 will scrape fluid off of the instrument. The fluid will naturally run outward toward the outer-most edges of the seal face 168.

Since the outer edges are in contact with the inner sidewall 169 of the proximal housing 6, the fluid will be wicked away from the seal face 168 and onto the inner sidewall 169 of the housing 6. While not shown, the housing 6 can optionally include an absorbent disposed therein for absorbing the fluid wicked away from the seal.

Figure 11:
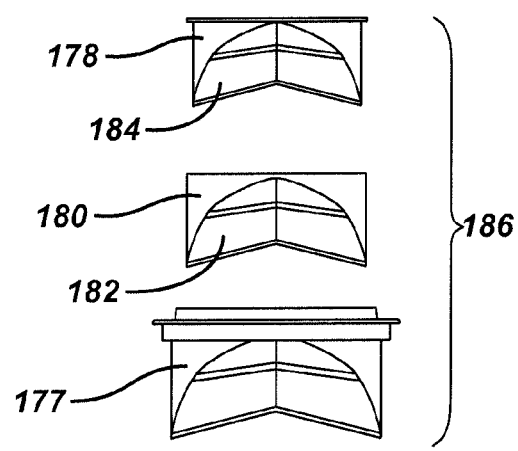
FIG. 11 is an exploded view of another embodiment of fluid remover assembly having an absorbent element nested between first and second zero-closure seals.

FIG. 11 illustrates another embodiment of a modified zero-closure seal 186. In this embodiment, an absorbent element 180 is nested inside of the duckbill seal 177, and a second duckbill seal 178 is nested within the absorbent element 180. The nested absorbent 180 and the nested duckbill seal 178 can have two sealing walls, 182, 184 similar to the duckbill seal 177, that meet at a seal face that is configured to form a seal when no instrument is disposed therein and that are configured to open when a surgical instrument is passed therethrough. The body of the nested absorbent 180 and the nested duckbill 178 can each have a profile similar or identical to the duckbill seal 177, except smaller in size to all fit for a nested configuration. The components 177, 178, 180 can merely be seated within one another, or they can be attached to one another using various attachment mechanisms known in the art, including a press fit, glue, etc. In use, the seal face of all three components will contact a surgical instrument as it is passed through the seal assembly. The absorbent 180 will thus absorb any fluid on the instrument, as well as fluid scraped off of the instrument by the duckbill seal 177 and the nested duckbill seal 178.

Figure 12A:
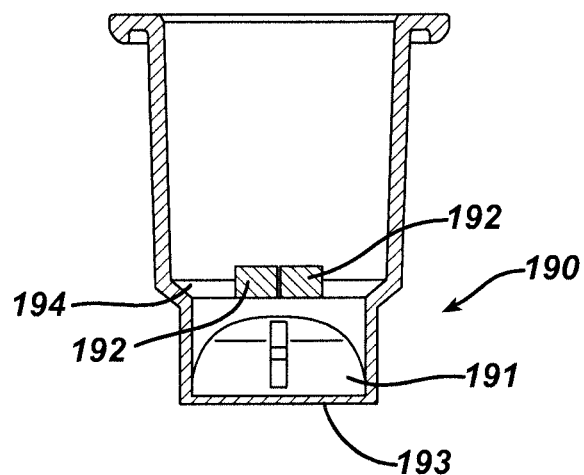
FIG. 12A is a cross-sectional view of yet another embodiment of an absorbent element having two absorbent bars disposed within a zero-closure seal.
Figure 12B:
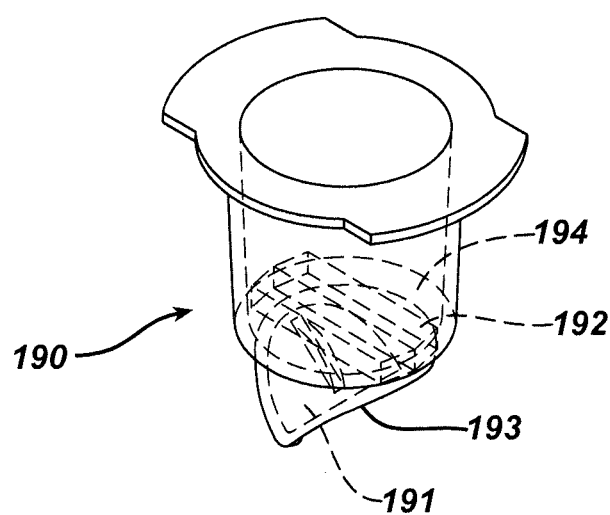
FIG. 12B is a transparent perspective view of the absorbent element and seal of FIG. 12A.

FIGS. 12A-12B illustrate another embodiment of a modified zero-closure seal 190. In this embodiment, the duckbill seal 191 includes two absorbent bars 192 disposed therein and extending thereacross. The absorbent bars 192 can be positioned to extend substantially parallel to the seal face 193, or to extend substantially perpendicular as shown. The seal 190 can also include an absorbent ring 194 positioned around an inner sidewall 193 of the duckbill seal 191 and in contact with the absorbent bars 192. The absorbent ring 194 can provide a reservoir for fluid collected by the absorbent bars 192. In use, the absorbent bars 192 will contact and engage a surgical instrument as it is passed through the duckbill seal 191, and will thus absorb fluid away from the surgical instrument.

As indicated above, the various fluid remover embodiments disclosed herein can be located anywhere within a trocar or other access device, including distal of a zero-closure seal, between a zero-closure seal and an instrument seal, or proximal of an instrument seal. The fluid removers can also be formed integrally with the seal(s) and/or portions of the housing, and any combination of fluid removers can be used. FIGS. 13-22B illustrate various exemplary embodiments of fluid removers that are formed integrally or incorporated into an instrument seal, or located adjacent to an instrument seal and thus proximal to a zero-closure seal.

Figure 13:
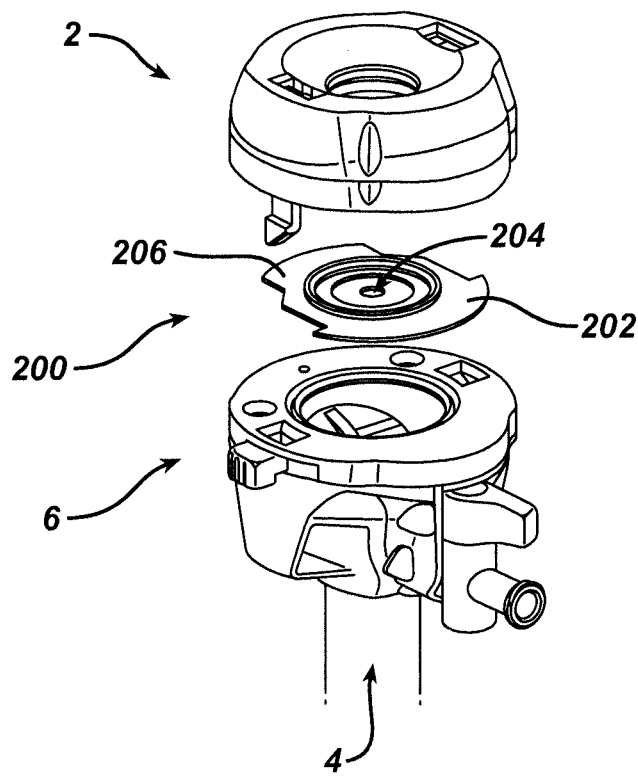
FIG. 13 is an exploded view of one embodiment of a trocar housing having a scraper for scraping fluid away from a surgical instrument passed therethrough.

Turning first to FIG. 13, in this embodiment the fluid remover 200 is in the form of a combination scraper and absorbent. In particular, the fluid remover 200 includes a generally planar circular scraper disc 202 having an opening 204 formed therethrough and configuration to be positioned coaxial with the working channel 4 in the trocar 2. The opening 204 can be sized and configured to form a seal around an instrument passed therethrough. The fluid remover 200 can also include an absorbent disk 206 disposed concentrically around the opening 204 in the scraper 202. In use, the scraper 202 will scrape fluid off of instruments passed therethrough, and the absorbent disk 206 will absorb the scraped fluid. The fluid remover 200 can be disposed within the proximal housing 6 of the trocar 2 using various techniques, but as shown in FIG. 13 the fluid remover 200 is configured to be engaged between the removable cap 5 and the distal portion of the proximal housing 6 of the trocar 2. As a result, the scraper 202 and absorbent 206 will be positioned in alignment with the working channel 4 extending through the housing 6, and will also be positioned between the proximal instrument seal and the distal zero-closure seal.

Figure 14:
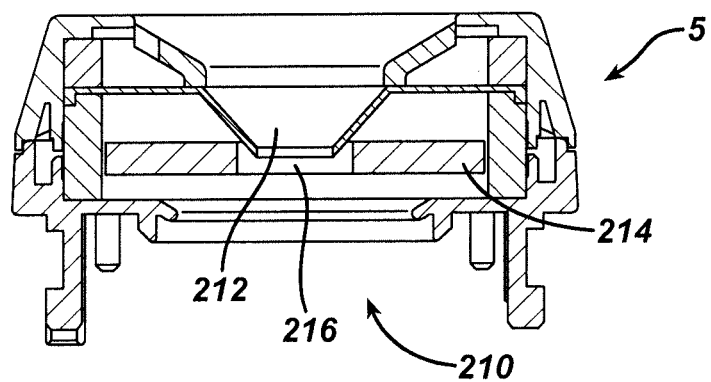
FIG. 14 is a cross-sectional view of one embodiment of a trocar cap having a scraper for scraping fluid away from a surgical instrument passed therethrough.

FIG. 14 illustrates another embodiment of a fluid remover 210 having a combination scraper and absorbent, however in this embodiment the fluid remover 210 is fully disposed within the removable cap 5 containing the instrument seal. As shown, a scraper 212 can be cone shaped and can be positioned just distal of the instrument seal. An absorbent ring 214 can be positioned concentrically around and in contact with an opening 216 in the distal end of the of the conical scraper 212. As a result, the absorbent ring 214 will absorb any fluid scraped away from a surgical instrument extending through the scraper 212.

Figure 15A:
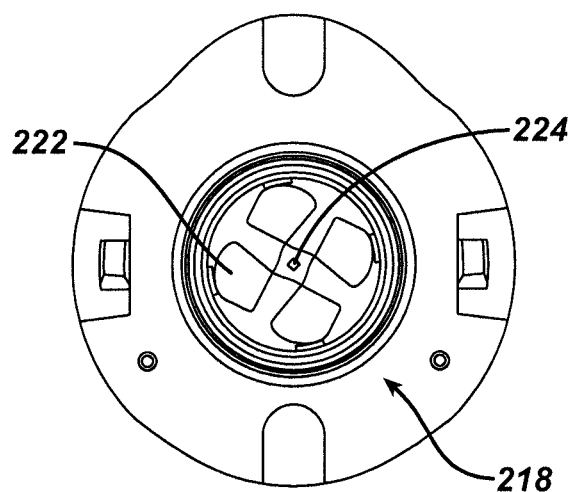
FIG. 15A is a top view of a trocar cap having another embodiment of a scraper for scraping fluid away from a surgical instrument passed therethrough.
Figure 15B:
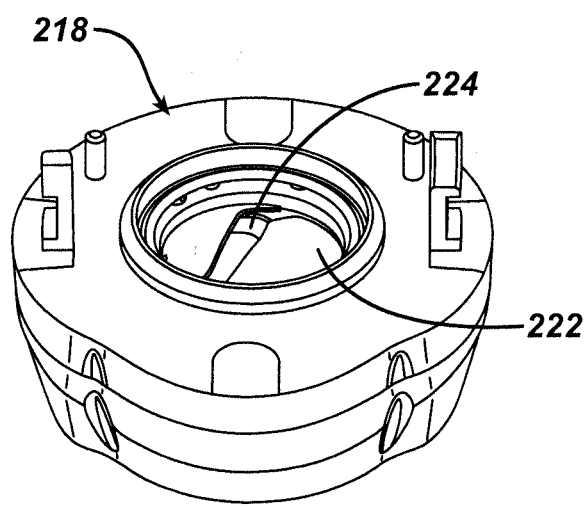
FIG. 15B is a side perspective view of the trocar cap of FIG. 15A.

In yet another embodiment, shown in FIGS. 15A and 15B, the fluid remover can be in the form of a scraper that is part of the instrument seal 218. As shown, the instrument seal 218 is a multi-layer seal having the protector disposed on a proximal surface thereof, as previously described with respect to FIG. 1E. The scraper can be in the form of a second protector 222 that is disposed distal to the multi-layer seal segments. The second protector 222 can have the same configuration as the protector of FIG. 1E, however the second protector 222 can define an opening 224 that is configured to contact and engage a surgical instrument passed through the seal 218. Accordingly, in use, the second protector 222 can engage and scrape fluid away from instruments passed through the seal 218.

Figure 16:
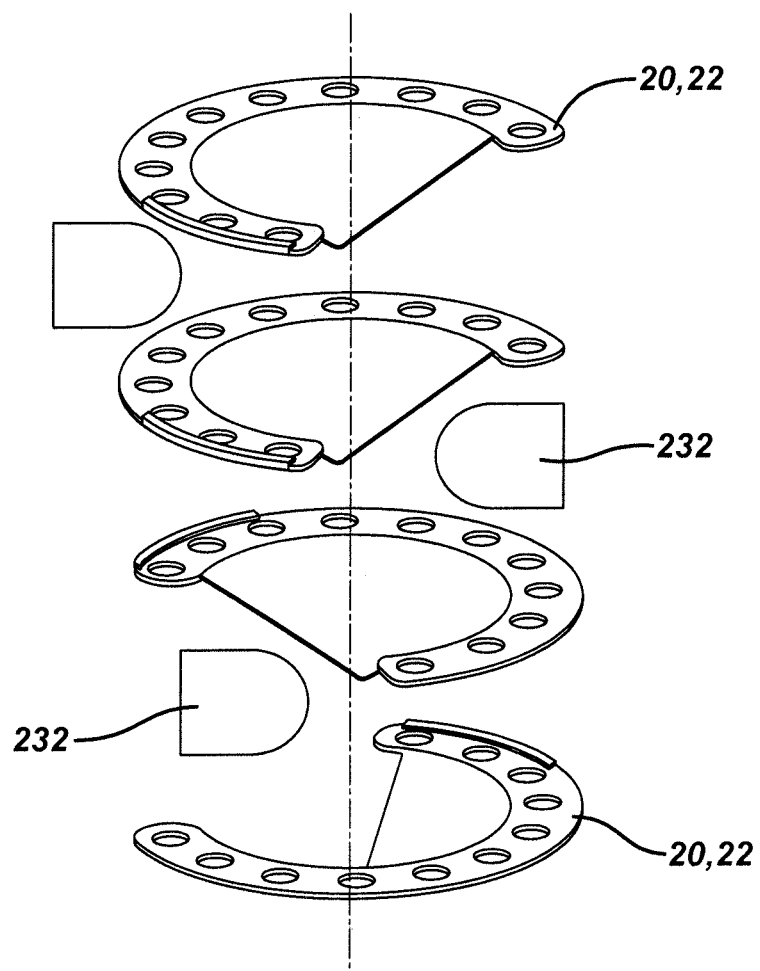
FIG. 16 is an exploded view of one embodiment of a multi-layer seal having an absorbent element disposed between the layers.

In another embodiment, shown in FIG. 16, the fluid remover can be in the form of a multi-layer absorbent that is positioned between the multiple layers 20 of the seal 16, as shown, or that is positioned between the multiple layers 22 of the seal protector 18. The absorbent can be in the form of multiple absorbent sheets 232 that are layered in between the layers of the seal 16 (or seal protector 18). Thus, in use, when an instrument is passed through the instrument seal, the sheets 232 will absorb any fluids scraped off of the instrument by the seal 14, thereby preventing fluid from accumulating around the opening of the seal 14 and being reapplied to a surgical instrument as it is reinserted therethrough. The absorbent sheets 232 can be effective to absorb fluid, as well as to interrupt surface tension and/or capillary action between the seal and the protector. Thus, there should be no fluid in or near the seal opening and/or protector opening that will be able to touch or collect on an instrument being passed therethrough.

Figure 17:
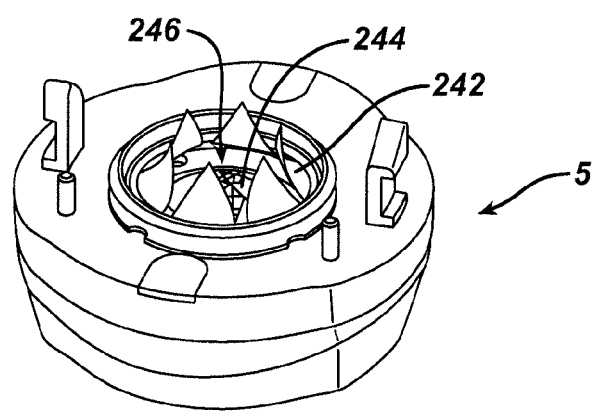
FIG. 17 is a bottom perspective view of one embodiment of a trocar cap having an absorbent element disposed therein.

FIG. 17 illustrates another embodiment of an absorbent fluid remover. In this embodiment, the absorbent is in the form of a grommet 242 having a configuration similar to the grommet 172 previously described with respect to FIG. 9. However, in this embodiment the grommet 242 is positioned adjacent to a distal surface 244 of the instrument seal 14, rather than the zero-closure seal 24. In particular, as shown in FIG. 17, the grommet 242 can be disposed concentrically around a distal opening 246 formed in the removable cap 5 such that instruments passed through the instrument seal 14 will contact the grommet 242, which will absorb fluids off of the instrument. The grommet 242 can also absorb any fluid that drips from the instrument seal 14.

Figure 18A:
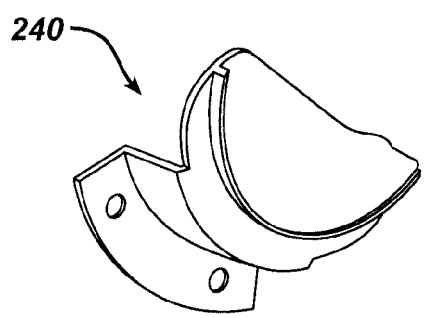
FIG. 18A is a bottom perspective view of one embodiment of a wicking element formed on a portion of a seal protector for creating between the seal protector and a seal.
Figure 18B:
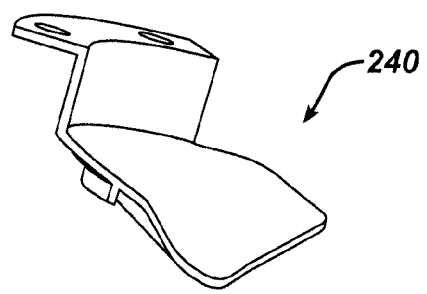
FIG. 18B is a top perspective view of the portion of the seal protector of FIG. 18A.

In another embodiment shown in FIGS. 18A and 18B, a wicking element is formed integrally with the multi-layer seal protector 18 previously described with respect to FIG. 1E. As previously explained, the multi-layer seal 16 can have a natural shape that is slightly conical and it can include an opening sized to receive an instrument therethrough. The protector 18 likewise has an opening, however in the embodiment shown in FIGS. 18A and 18B the length of a protector 240 is decreased to thereby increase the diameter of the opening defined by the protector 18. As a result, the protector 240 will have an opening that is larger than the opening in the seal 16 to create a flattened profile against the conical shape of the seal 16, thereby creating a gap between the protector 240 and seal 16. As surgical instruments are removed from the trocar, the gap will prevent fluids from collecting between the layers 20 of the seal 16 and will allow the protector 240 to wick fluids away from the opening of the seal 16. Thus, if fluid is deposited on the sea 16, there will be no capillary action to hold the fluid between the seal 16 and the protector 240, thereby allowing the fluids to drain. In addition, when an instrument is passed through the protector 240 and seal 16, the gap created between the seal 16 and protector 18 will prevent fluid from being squeezed from between the seal 16 and protector 240 and onto an instrument.

Figure 19A:
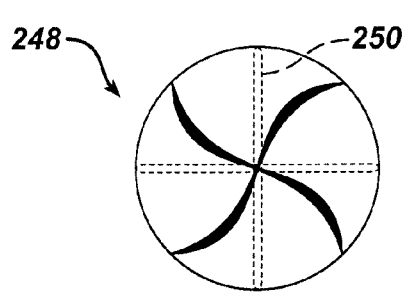
FIG. 19A is a top view of a multi-layer protective member having camming ribs.
Figure 19B:
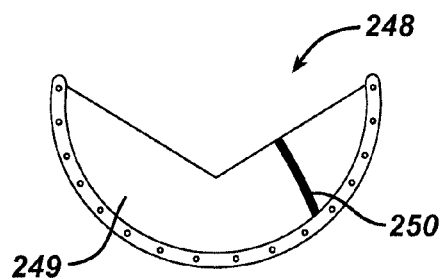
FIG. 19B is a top view of one layer of the protective member of FIG. 19A.

In another embodiment shown in FIGS. 19A and 19B, the multi-layer seal protector 248 has a wicking element in the form of camming ribs 250 disposed on a surface of each individual protector layer 249 so that the ribs 250 create pockets between the layers for wicking away and retaining fluid scraped off of instruments by the instrument seal. In the illustrated embodiment, the ribs 250 are offset by 90 degrees, although other geometries are possible as will be appreciated by those skilled in the art. In one embodiment, the ribs 250 can be disposed on a top or proximal surface of the protector. Thus, as a surgical instrument is passed through the instrument seal 14, the instrument will contact the ribs 250 to thereby cam open the protector 248 and the seal, preventing the surgical instrument from coming into contact with the surface of the protector 248 and/or the seal. In another embodiment, the ribs 250 can be disposed on a bottom or distal surface of the protector, thereby creating a gap between the protector 248 and the seal to prevent capillary action and the trapping of fluid between the seal and protector 248.

Figure 20A:
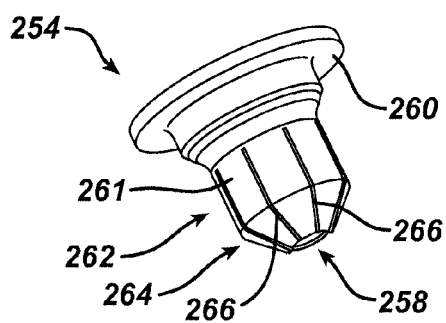
FIG. 20A is a side perspective view of a deep cone instrument seal having camming ribs formed on an external surface.
Figure 20B:
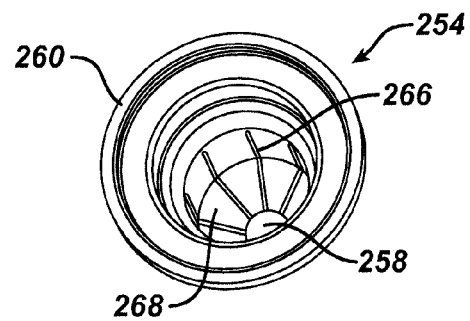
FIG. 20B is a top perspective view of another embodiment of a deep cone instrument seal having camming ribs formed on an internal surface.

FIGS. 20A and 20B illustrate another embodiment of an instrument seal 254 having ribs for wicking fluid away from an opening in the seal 254. In this embodiment, the instrument seal 254 is in the form of a deep cone seal having a flange 260 with a conical sidewall 262 extending distally therefrom. A distal portion 264 of the conical sidewall 262 tapers inward to define an opening 258 in the distal end 264 of the seal 254. In the embodiment shown in FIG. 20A, the sidewall 262 can include one or more ribs 266 formed on an external surface 261 thereof and extending between proximal and distal ends of the sidewall 262, terminating at the opening 258. The external ribs 266 can be effective to wick fluid away from the opening 258 in the seal 254. In the embodiment shown in FIG. 20B, the ribs 266 are formed on the inner surface 268 of the sidewall 262 and extend between proximal and distal ends of the sidewall 262, terminating at the opening 258. The ribs 266 will thus have a camming effect, causing any instrument inserted through the seal 254 to contact the ribs 266 to cam open the seal 254, rather than contacting an inner surface 268 of the seal 254.

Figure 21:
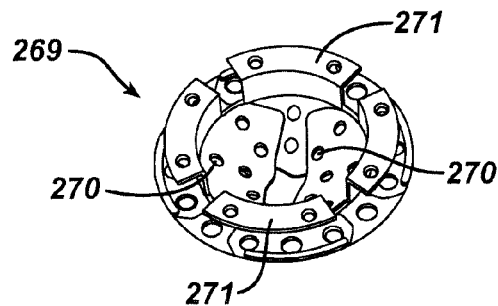
FIG. 21 is a perspective view of a multi-layer protective element having holes formed therein for receiving fluid.

In another embodiment, shown in FIG. 21, the multi-layer seal protector 269 can include a plurality of holes 270 formed in the individual layers 271 of the protector 269 to form a wicking element for wicking fluid away from the seal. As fluid is trapped between the protector 269 and the seal when an instrument is passed through the instrument seal, the holes 270 act to wick away fluid from the seal and from the opening in the seal. The fluid can be retained within the holes 270 by surface tension so that an instrument passed through the seal will not contact the fluid retained in the holes 270.

Figure 22A:
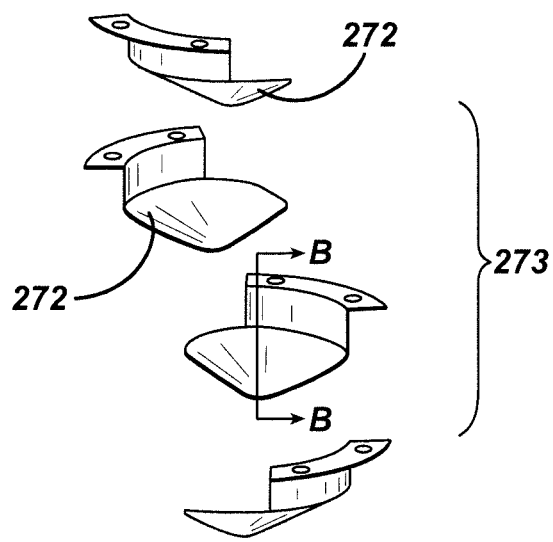
FIG. 22A is an exploded view of a multi-layer protective element.
Figure 22B:
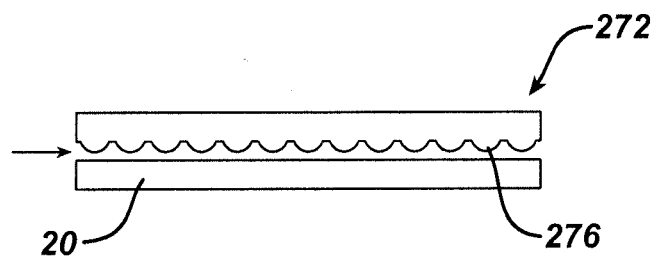
FIG. 22B is a cross-sectional view taken across line B-B of one of the protective elements of FIG. 22A.

Various other modifications can also be made to the multi-layer seal protector previously described in FIG. 1E to remove fluid from the seal or from instruments passed through the seal. In another embodiment, shown in FIGS. 22A and 22B, the protector segments 272 can include surface features, such as a roughened surface 276, formed on the distal surface thereof. As shown in FIG. 22B, when the protector segments 272 are positioned against the seal segments 20, the roughened surface 276 will create a gap that separates the protector 273 from the seal, thus providing a path for fluid to wick away from the opening in the seal and from between the protector 273 and the seal.

Figure 23A:
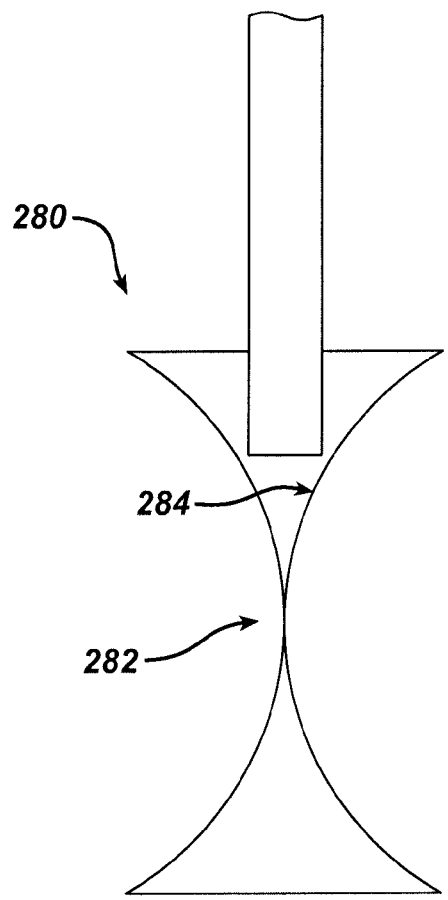
FIG. 23A is a side view of one embodiment of a seal having an hourglass configuration for scraping fluid off of a surgical instrument.
Figure 23B:
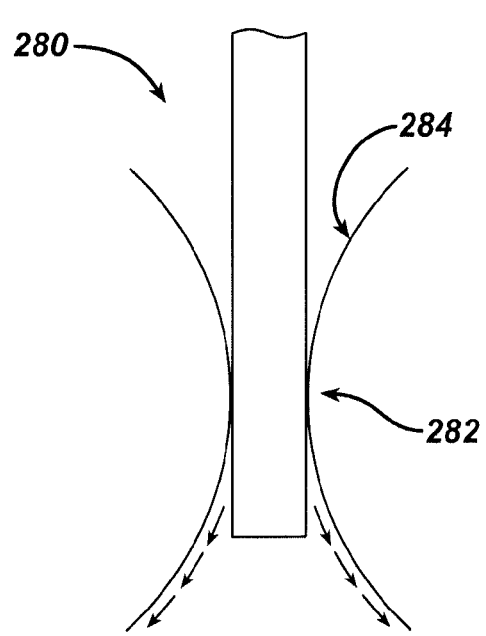
FIG. 23B is a side view of the seal of FIG. 23A showing an instrument passed therethrough.

FIGS. 23A-23B illustrate another embodiment of a seal 280 that is configured to remove fluid. In this embodiment, the seal 280 has an hourglass configuration such that the seal 280 is a combination trocar and instrument seal. In other words, the seal 280 is effective to both form a seal within the working channel of the trocar when no instrument is disposed therethrough and to form a seal around an instrument disposed therethrough. The hourglass shape of the seal 280 allows a central portion 282 of the seal 280, which in a natural state is in a closed configuration as shown in FIG. 23A, to open and engage an instrument passed therethrough, as shown in FIG. 23B, and thereby scrape any fluid off of the instrument. Due to the curvature in inner sidewalls 284 of the seal 280, the removed fluid will flow away from the central portion thus preventing the fluid from being redeposited onto an instrument reinserted therethrough. The hourglass configuration of the seal 280 is also advantageous in that it will accommodate instruments of various sizes. The central portion 282 can also move or float relative to the central axis of the working channel in the trocar, thus accommodating off-axis instruments.

FIGS. 24A-29 illustrate various other exemplary embodiments of fluid removers. While certain embodiments are described as being disposed or formed in the cannula, a person skilled in the art will appreciate that, as with previous embodiments, the embodiments of FIGS. 24A-29 can likewise be disposed at various locations within a trocar and that various combinations of fluid removers can be used.

Figure 24A:
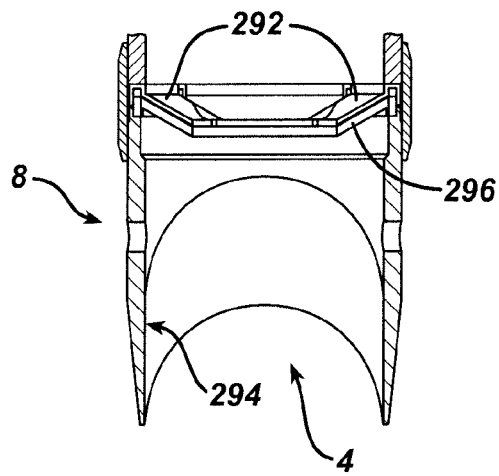
FIG. 24A is cross-sectional view of one embodiment of a trocar cannula having overlapping scrapers and an absorbent disposed therein.
Figure 24B:
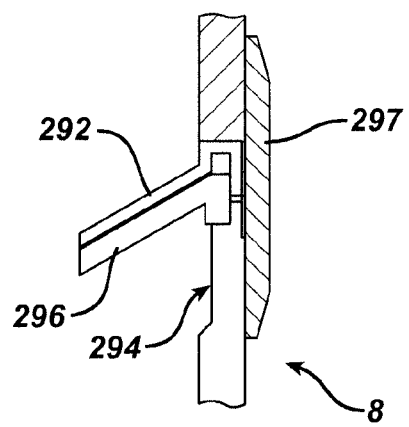
FIG. 24B is an enlarged view of one of the scrapers and absorbents of FIG. 24A.

In the embodiment shown in FIGS. 24A and 24B, the fluid remover is in the form of a plurality of scraper elements that extend at least partially across the working channel 4 of the cannula 8. The scraper elements can be relatively thin and can take the shape and form of wipers 292, as best shown in FIG. 24B, that will scrape or squeegee fluid off of a surgical instrument passed through the cannula 8. The wipers 292 can be fixedly or hingedly coupled to an inner sidewall 294 of the cannula 8, and they can be flexible to accommodate instruments of various sizes, and to allow both insertion and withdrawal of the instruments. The cannula 8 can also include any number of wipers 292, and the wipers 292 can be spaced apart from one another, or they can be in a stacked configuration. The wipers 292 can have a conical configuration such that each wiper 292 extends around the entire inner diameter of the cannula 8. Alternatively, the wipers 292 can be formed into individual segments that are positioned a distance apart from one another, e.g., approximately 90 degrees apart within the interior surface 294 of the cannula 8. The segments can be layered within the cannula 8 so that different parts of the surgical instrument come into contact with the wipers 292 at different heights as the instrument is being passed therethrough. The wipers 292 can also be in contact with an absorbent element 296, or include an absorbent portion, such that the collected fluid drips onto or is wicked into the absorbent material and away from possible contact with a reinserted instrument. As shown in FIGS. 24A-24B, the absorbent element 296 is located adjacent to the inner sidewall 294, and thus radially outward from the wiper body 292. The absorbent elements 296 can be formed into a wall of the cannula 8, so that the cannula 8 is partially formed from the absorbent elements 296. The absorbent elements 296 can also be formed within grooves in the cannula wall and/or can be adhered directly to the cannula wall by any attachment mechanism known in the art, for example an attachment ring 297. In use, as an instrument is passed through the cannula 8, the instrument will be scraped on all sides simultaneously by the plurality of wipers 292. The fluid will flow outward where it will be absorbed by the absorbent element 296.

Figure 25:
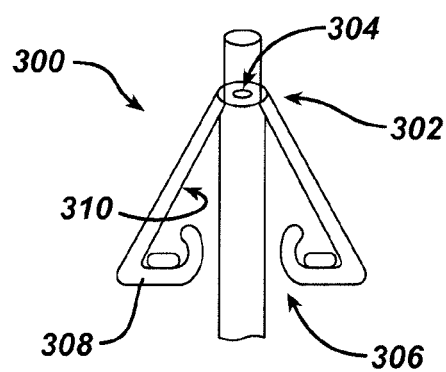
FIG. 25 is a perspective view of another embodiment of a scraper for scraping fluid off of a surgical instrument shown passed therethrough.

FIGS. 25 illustrates another exemplary embodiment of a scraper 300. In this embodiment, the scraper 300 is substantially cone shaped increasing in diameter in a distal direction. A proximal end 302 of the scraper 300 includes an opening 304 formed therethrough, and a fluid collection member is formed at a distal end 306 thereof and extends inwardly. The fluid collection member can have a variety of configurations and can be generally configured to collect fluid scraped by the scraper 300. In one exemplary embodiment, as shown, the fluid collection member can be in the form of a substantially C-shaped lip 308 extending inwardly from the distal end 306 of the scraper 300. At least a portion of the fluid collection member can also optionally be absorbent thereby enabling the fluid collection member to both collect and absorb fluid scraped by the scraper. The scraper 300 can be formed from a pliable material such that it can radially expand to engage a surgical instrument extending therethrough. In use, the narrow proximal end of the scraper 300 can engage a surgical instrument passed therethrough to thereby scrape fluid away from the instrument. The fluid scraped away from the instrument will run down an inner surface 310 of the scraper 300 and be collected and/or absorbed by the fluid collection member disposed at the distal end 306 of the scraper 300. While the scraper 300 is generally indicated as being disposed in the cannula 8, the scraper 300 can likewise be disposed anywhere within the trocar 2, including in the proximal housing 6.

Figure 26:
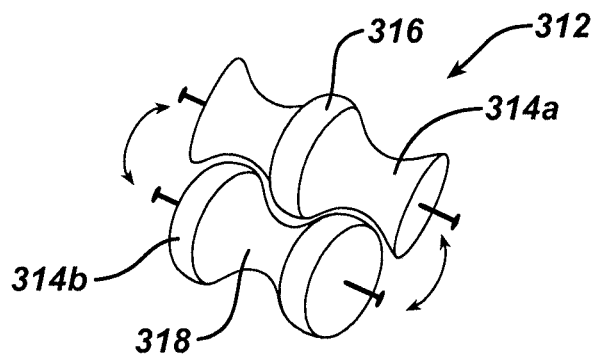
FIG. 26 is a perspective view of another embodiment of a device for scraping fluid away from a surgical instrument.

FIG. 26 illustrates another exemplary embodiment of a scraper 312. In this embodiment, the scraper 312 includes first and second rotatable members 314a, 314b that are configured to rotate and engage a surgical instrument as the instrument is passed therethrough. The first and second rotatable members 314a, 314b can have a variety of shapes and sizes. In the illustrated embodiment, the first and second rotatable members 314a, 314b are spool shaped. The spools can be configured such that the geometry of second member 314b complements that of the first member 314a. As shown, the first member 314a includes a substantially spherically shaped central portion 316 that corresponds with a concave cut-out 318 in the second member 314b. The geometry of the spools can have several shapes including, but not limited to, straight sided cylindrical, c-shaped, and indented cylindrical. The first and second rotatable members 314a, 314b can be positioned at a variety of locations in the cannula, or within the proximal housing of a trocar, and they can be formed from a variety of materials including, but not limited to, rigid, pliable, and absorbent materials. In use, the rotatable members 314a, 314b can rotate and engage a surgical instrument passed therethrough to thereby scrape and optionally absorb fluid away from the instrument.

Figure 27A:
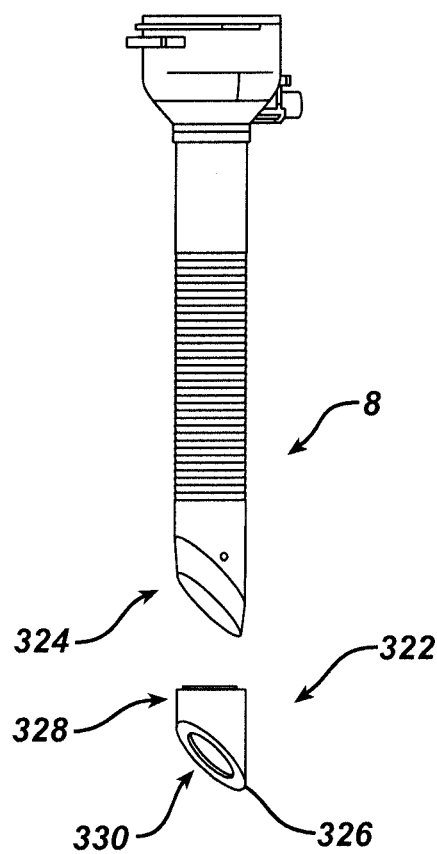
FIG. 27A is an exploded view of a trocar and removable cap for scraping fluid away from a surgical instrument.
Figure 27B:
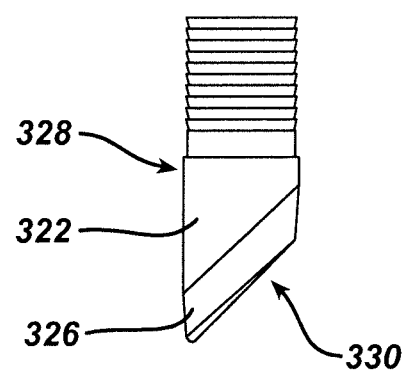
FIG. 27B is an assembled side view of a distal end of the trocar and removable cap of FIG. 27A.
Figure 27C:
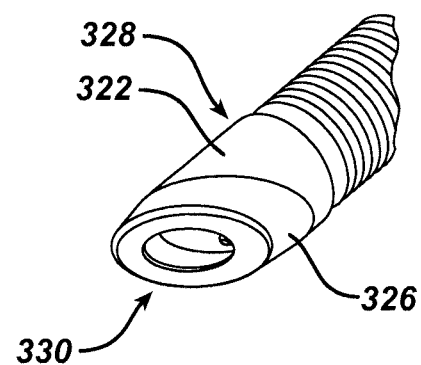
FIG. 27C is a perspective view of the removable cap and distal end of the trocar of FIG. 26B.

FIGS. 27A-27C illustrate another embodiment of a fluid remover in the form of a sleeve 322 that can be removable coupled to a distal end 324 of the cannula 8. As shown, the sleeve 322 is in the form of a generally cylindrical housing with a tapered distal end 326, similar to the distal end 324 of the cannula 8. A proximal end 328 of the sleeve 322 can be sized to fit over and engage the distal end of the cannula 8, e.g., by interference fit, and the distal end of the housing can include an opening 330 formed therein and sized to receive a surgical instrument therethrough. The sleeve 322, or at least a portion of the sleeve 322 surrounding the opening 330 at the distal end 326, can be formed from a compliant or expandable material to allow the opening in the sleeve 322 to radially expand as an instrument is passed therethrough. Exemplary compliant materials include, but are not limited to, polyisoprene, pellathane, and silicone. In use, as a surgical instrument is passed through the opening 330 in the sleeve 322, the opening 330 will scrape fluid off of the instrument, thereby preventing the fluid from being dragged into the trocar and deposited on the seals.

Figure 28:
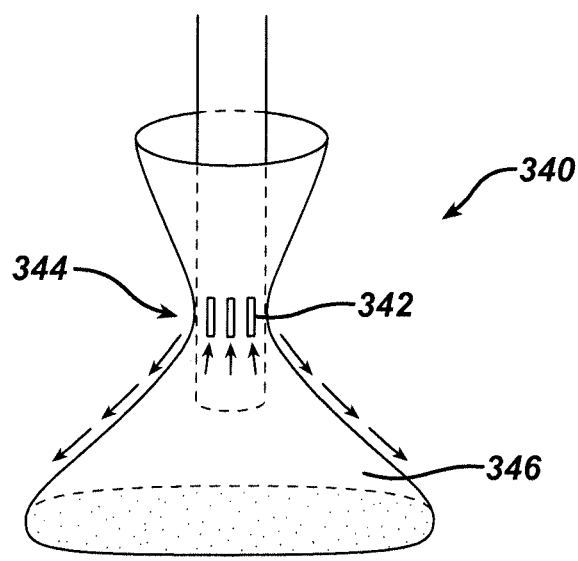
FIG. 28 is a partially-transparent side view of one embodiment of wicking element having an hourglass shape.

In another embodiment shown in FIG. 28, an hourglass shaped seal 340, similar to the seal 280 described with respect to FIGS. 23A-23B is provided, however the seal 340 includes a wicking element in the form of one or more cut-outs or slots 342 formed in the central, reduced-diameter portion 344. Similar to the seal 280 previously described with respect to FIG. 23A and 23B, the hourglass shape will allow the central portion 344 to scrape or squeegee fluid from a surgical instrument passed therethrough. The cut-outs or slots 342 will allow the scraped fluid to be wicked through the slots 342 to an exterior surface 346 of the seal 340.

Figure 29:
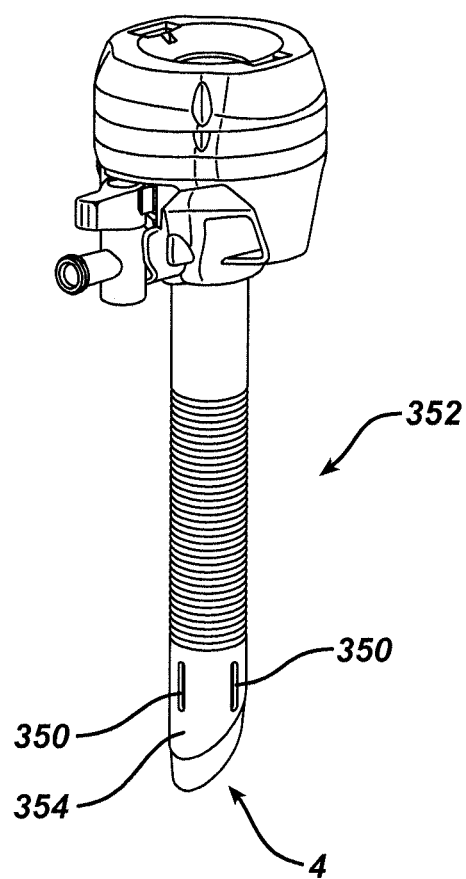
FIG. 29 is a perspective view of a trocar having a cannula with slots formed therein for wicking fluid out of the cannula.

In another embodiment shown in FIG. 29, the wicking element can take the form of a plurality of slots 350 formed in the working channel 4 of a cannula 352. The slots 350 can have any size and shape sufficient to transfer fluid disposed on an inner surface of the cannula 352 to an outside surface 354 of the cannula 352. Thus, as an instrument is passed through the cannula 352, any fluid that drips down the inner surface of the cannula 352 will be transferred to the external surface 354 of the cannula 352 through the slots 350.

All of the above described fluid remover embodiments can be formed into a single "drop-in" unit as needed. The drop-in unit can include absorbent elements, scraper elements, wicking elements, and/or combinations thereof. These elements can be combined as needed into an externally configured unit that can be placed into an existing trocar system as needed. Thus, the drop-in unit will fit in and around any seals and components disposed within the proximal housing, including the removable cap, and/or within the cannula. For example, the drop-in unit can be configured to fit below or distal to one or more sealing elements and/or it can be configured to fit above or proximal to one or more sealing elements. Alternatively or in addition, the drop-in unit can be configured to have components that fit above, below, or in between sealing elements. The drop-in unit can also be removable as needed.

Methods for removing fluid from a surgical instrument are also provided. In an exemplary embodiment, a surgical instrument can be passed through an access device and a fluid remover in the access device can remove any fluid on the instrument, or fluid deposited on a seal within the access device by the instrument. In one exemplary embodiment, a fluid remover can engage a surgical instrument passed through an access device, such as a trocar, upon removal of the instrument to thereby removes fluid from the instrument, thus preventing the fluid from accumulating on the seal(s) and/or from being redeposited on instruments passing therethrough. As indicated above, the fluid remover can be formed from any combination of one or more absorbing, scraping, and wicking elements. A person skilled in the art will appreciate that virtually any combination of absorbing, scraping, and wicking elements can form the fluid remover resulting in a variety of methods for removing fluid that can include any combination of absorbing, scraping, and wicking fluid away from a surgical instrument and/or from a seal or other portion of a trocar or other access device.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical access device, comprising:
   a housing having a cannula extending distally therefrom;
   a first seal disposed within the housing and configured to receive a surgical instrument therethrough, and to form a seal around a surgical instrument disposed therethrough; and
   a second seal disposed within the housing and separate and detached from the first seal, the second seal being configured to form a seal when no surgical instrument is disposed therethrough; and
   a scraper disposed within the housing and positioned distal to the first and second seals and configured to scrape fluid off of a surgical instrument extending through the first and second seals and the scraper, the scraper having a central opening and capillary channels formed on a distal surface thereof, disassociated from the central opening and extending radially outward from the central opening.

2. The surgical access device of claim 1, wherein the scraper is positioned a distance apart from the first and second seals.

3. The surgical access device of claim 1, wherein the first seal comprises an instrument seal having an opening formed therethrough and configured to form a seal around a surgical instrument disposed therethrough, and wherein the second seal comprises a zero-closure seal configured to form a seal when no surgical instrument is disposed therethrough.

4. The surgical access device of claim 3, further comprising a second scraper positioned between the instrument seal and the zero-closure seal.

5. The surgical access device of claim 1, wherein the scraper comprises first and second rotatable members configured to rotate as a surgical instrument is passed therethrough.

6. The surgical access device of claim 1, wherein at least one of the first and second seals is substantially conical shaped and includes a protector disposed proximal thereto.

7. The surgical access device of claim 6, wherein the protector and the at least one of the first and second seals each include multiple layers.

8. The surgical access device of claim 1, wherein the scraper is substantially cone shaped.

9. The surgical access device of claim 1, wherein the scraper includes at least one slit formed therein and configured to allow the scraper to radially expand.

10. The surgical access device of claim 1, wherein an inner portion of the scraper includes a fluid collection member configured to collect fluid scraped by the scraper.

11. The surgical access device of claim 10, wherein the fluid collection member comprises a substantially C-shaped lip.

12. The surgical access device of claim 10, wherein at least a portion of the fluid collection member is sorbent.

13. The surgical access device of claim 1, wherein at least a portion of the scraper is adapted to sorb fluid.

14. A surgical access device, comprising:
   a housing defining a working channel sized and configured to receive a surgical instrument;
   a cannula extending distally from the housing configured for receiving a surgical instrument inserted through the housing;
   a seal assembly disposed in the housing for forming a seal around a surgical instrument disposed through the working channel and forming a seal in the working channel when no surgical instrument is disposed through the working channel;
   a scraping element disposed in the housing and positioned distal to the seal assembly, the scraping element having a central opening, and the scraping element being configured to scrape fluid off of a surgical instrument passed through the working channel and through the central opening, and the scraping element having radially-oriented elongate capillary grooves disassociated from the central opening; and
   a lid positioned distal of the seal assembly and seated on a proximal surface of the scraping element, the lid having an unobstructed opening formed therein, wherein a diameter of the opening of the lid is greater than a diameter of the central opening in the scraping element.

15. The surgical access device of claim 14, wherein the seal assembly includes a first seal having an opening configured to form a seal around a surgical instrument disposed therethrough, and a second seal configured to form a seal in the working channel of the housing when no instrument is disposed therethrough.

16. The surgical access device of claim 15, further comprising a second scraping element positioned between the first and second seals.

17. The surgical access device of claim 14, wherein the seal assembly comprises a single seal configured to both form a seal around a surgical instrument disposed through the working channel and form a seal in the working channel when no surgical instrument is disposed through the working channel.

18. The surgical access device of claim 14, wherein the scraping element is expandable.

19. The surgical access device of claim 14, wherein the scraping element comprises first and second rotatable members configured to rotate as a surgical instrument is passed therethrough.

20. The surgical access device of claim 14, wherein the scraping element is substantially cone shaped.

21. The surgical access device of claim 14, wherein at least a portion of the scraping element is sorbent.

22. The surgical access device of claim 16, wherein the second scraping element is disposed in a removable cap of the housing.

23. The surgical access device of claim 14, wherein an inner portion of the scraping element includes a fluid collection member configured to collect fluid scraped by the scraping element.

24. A surgical access device, comprising:
a housing having a cannula extending distally therefrom, the housing and cannula defining a working channel extending therethrough, and the housing having a distal portion and a proximal cap portion that is removably coupled to the distal portion;
an instrument seal disposed within the proximal removable cap portion of the housing, the instrument seal having an opening formed therethrough and configured to form a seal around a surgical instrument disposed therethrough;
a zero-closure seal disposed within the distal portion of the housing and positioned distal of the instrument seal, the zero-closure seal being configured to form a seal across the working channel when no surgical instrument is disposed therethrough;
a lid disposed within the distal portion of the housing and positioned distal of the zero-closure seal; and
a scraper disposed within the distal portion of the housing and fixedly positioned distal of the lid, the scraper having a plurality of channels extending only partially into a terminal, distal-facing surface thereof and configured to scrape fluid off and wick fluid away from instruments passed through the scraper.

25. The device of claim 24, wherein the scraper is part of a fluid remover assembly positioned distal of the lid.

26. The device of claim 25, wherein the fluid remover assembly includes a sorbent element and a wicking element.

27. The device of claim 24, wherein the plurality of channels extend radially outward from a central opening in the scraper.

* * * * *